(12) United States Patent
Karakaya et al.

(10) Patent No.: US 10,682,048 B2
(45) Date of Patent: Jun. 16, 2020

(54) DEVICE AND SYSTEM FOR MONITORING AN EYE OF A SUBJECT

(71) Applicant: KONINKLIJKE PHILIPS N.V., Eindhoven (NL)

(72) Inventors: Koray Karakaya, Eindhoven (NL); Charles Frederik Sio, Eindhoven (NL); Louis Nicolas Atallah, Boston, MA (US); Kiran Hamilton J. Dellimore, Ut (NL); Ron Martinus Laurentius Van Lieshout, Geldrop (NL); Susanne Maaike Valster, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 117 days.

(21) Appl. No.: 15/750,540

(22) PCT Filed: Aug. 5, 2016

(86) PCT No.: PCT/EP2016/068794
§ 371 (c)(1),
(2) Date: Feb. 6, 2018

(87) PCT Pub. No.: WO2017/025475
PCT Pub. Date: Feb. 16, 2017

(65) Prior Publication Data
US 2018/0235456 A1 Aug. 23, 2018

(30) Foreign Application Priority Data

Aug. 7, 2015 (EP) .................................. 15180180

(51) Int. Cl.
*A61B 3/12* (2006.01)
*A61B 3/00* (2006.01)
(Continued)

(52) U.S. Cl.
CPC ............ *A61B 3/0008* (2013.01); *A61B 3/103* (2013.01); *A61B 3/112* (2013.01);
(Continued)

(58) Field of Classification Search
CPC .............. A61B 3/112; A61B 3/12; A61B 3/13
(Continued)

(56) References Cited

U.S. PATENT DOCUMENTS 6,120,460 A 9/2000 Abreu
2006/0183986 A1 8/2006 Rice et al.
(Continued)

FOREIGN PATENT DOCUMENTS

EP 0050983 A2 5/1982
EP 0686372 A1 12/1995
(Continued)

OTHER PUBLICATIONS

Amos et al: "Photodetector Arrays Directly Assembled Onto Polymer Substrates From Aqueous Solution"; J. Am. chem. soc. vol. 129, No. 46, 2007, pp. 14297-14302.
(Continued)

*Primary Examiner* — Hung X Dang
(74) *Attorney, Agent, or Firm* — Daniel H. Brean

(57) ABSTRACT

The present invention relates to a device for monitoring an eye of a subject, comprising: a transparent carrier for being in contact with the eye of the subject; and a photosensor facing the eye of the subject for receiving light reflected from the eye of the subject and for determining a light intensity of the received light, wherein the photosensor is arranged on the transparent carrier; and wherein the photosensor includes one of: a plurality of photodetectors arranged in the form of a two-dimensional array and spaced apart from one another for allowing incident light to pass between the photodetectors to enter the eye of the subject
(Continued)

(a)

(b)

wherein the plurality of photodetectors is arranged in a plurality of rows of photodetectors or in a plurality of concentric circles substantially covering the iris and the pupil of the eye of the subject; and a single large area photodetector covering an iris and a pupil of the eye of the subject. The present invention further relates to a system and method for monitoring a pain level of a subject comprising a device as defined above.

15 Claims, 10 Drawing Sheets

(51) Int. Cl.
  A61B 3/11   (2006.01)
  A61B 5/1455 (2006.01)
  A61B 5/00   (2006.01)
  A61B 3/103  (2006.01)
(52) U.S. Cl.
  CPC ........ A61B 5/14551 (2013.01); A61B 5/4821 (2013.01); A61B 5/4824 (2013.01); A61B 5/6821 (2013.01); A61B 2560/0214 (2013.01); A61B 2562/046 (2013.01)
(58) Field of Classification Search
  USPC .......... 351/219, 246, 159.03, 159.02, 159.01
  See application file for complete search history.

(56) References Cited

U.S. PATENT DOCUMENTS

| 2014/0185010 A1 | 7/2014 | Bernert et al. |
| 2014/0240665 A1 | 8/2014 | Pugh et al. |
| 2014/0268014 A1* | 9/2014 | Pugh ........................ G02C 7/04 351/158 |
| 2014/0277291 A1 | 9/2014 | Pugh et al. |
| 2015/0087249 A1 | 3/2015 | Pugh et al. |

FOREIGN PATENT DOCUMENTS

| EP | 2508935 A1 | 10/2012 |
| EP | 2609852 B1 | 9/2014 |
| WO | 2014186501 A1 | 11/2014 |

OTHER PUBLICATIONS

Bergamin et al: "Latency of the Pupil Light Reflex:Samply Rate, Stimulus Intensity, and Variation in Normal Subjects"; Investigative Ophthalmology & Visual Science, Apr. 2003, vol. 44, No. 4, pp. 1546-1554.
Ellermeier et al: "Gender Differences in Pain Ratings and Pupil Reactions to Painful Pressure Stimuli"; Pain, 61 (1995), pp. 435-439.
Hofle et al: "You Can See Pain in The Eye: Pupillometry as an Index of Pain Intensity Under Differenct Luminance Conditions"; International Journal of Psychophysiology 70 (2008), pp. 171-175.
"Neuroptics/The Smart Approach to PupillaryEvaluation"; Avertisement for Company Neruoptics, Originally Downloaded From http://www.neuroptics.com/index.php?page=critical care on Oct. 9, 2014, 9 Page Document.
Nowak et al: "System and Measurement Method for Binocular Pupillometry to Study Pupil Size Variability"; Biomedical Engineering Online, 2014, 13:69, 16 Page Document.
Dirkes et al: "Pain Monitoring 2.0"; Philips Project Amore, 2014, pp. 1-41.
Pyati et al: "Perioperative Pain Management"; CNS Drugs 2007, vol. 21(3): pp. 185-211.
Stomberg et al: "Assessing Pain Responses During General Anesthesia"; AANA Journal, Jun. 2001, vol. 69, No. 3, pp. 218-222.

* cited by examiner

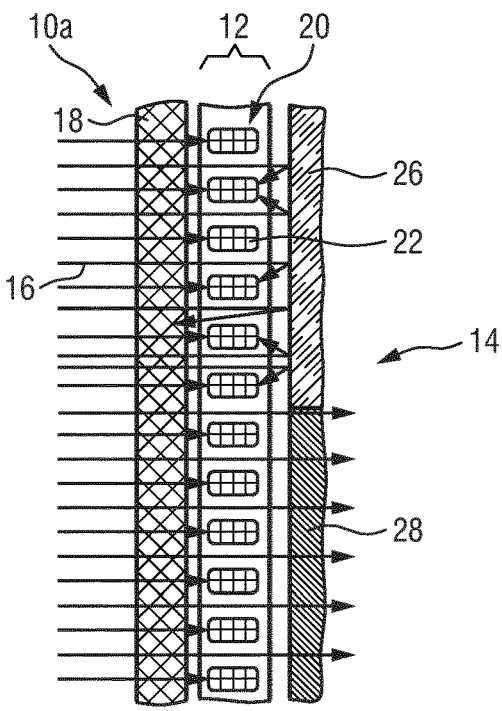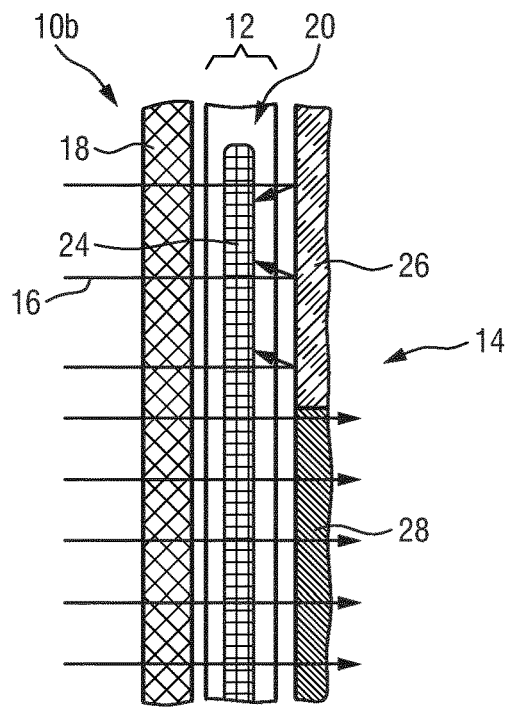
(a)  (b)
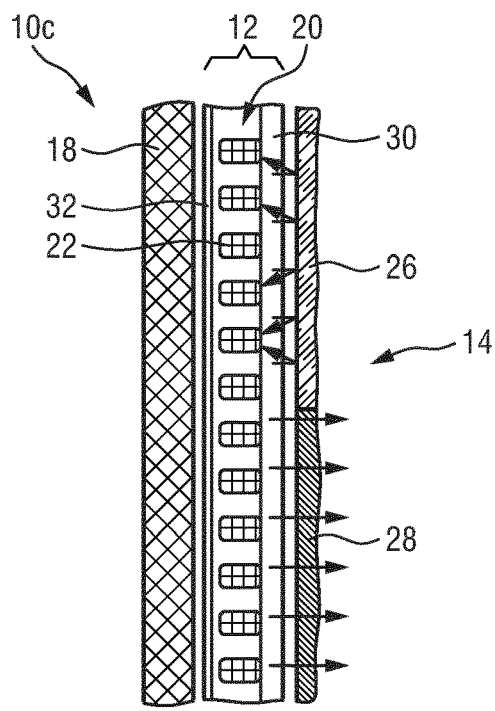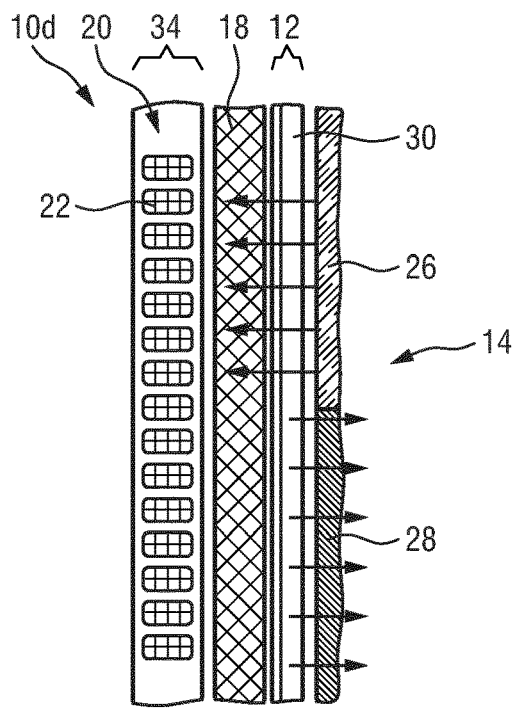
(c)  (d)
FIG.1

| INDEX | CONDITION | SCORE |
|---|---|---|
| SYSTOLIC BLOOD PRESSURE (mm HG) | LESS THAN CONTROL +15<br>LESS THAN CONTROL +30<br>MORE THAN CONTROL +30 | 0<br>1<br>2 |
| HEART RATE (beats/min) | LESS THAN CONTROL +15<br>LESS THAN CONTROL +30<br>MORE THAN CONTROL +30 | 0<br>1<br>2 |
| SWEAT | NIL<br>SKIN MOIST TO TOUCH<br>VISIBLE BEADS OF SWEAT | 0<br>1<br>2 |
| TEARS OR LACRIMATION | NO EXCESS TEARS WITH EYELIDS OPEN | 0 |
| | EXCESS TEARS VISIBLE WITH EYELIDS OPEN | 1 |
| | TEAR OVERFLOW FROM CLOSED EYELIDS | 2 |

FIG.4

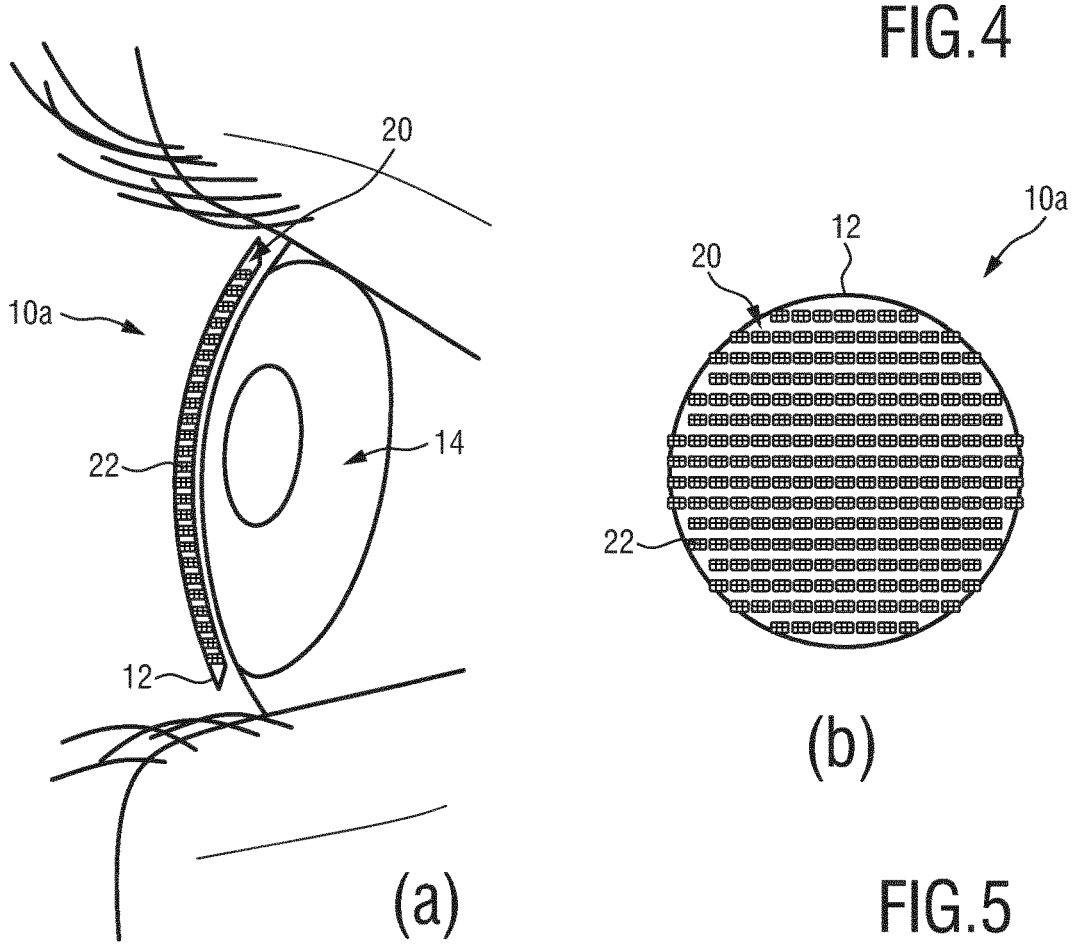

DEVICE AND SYSTEM FOR MONITORING AN EYE OF A SUBJECT

CROSS-REFERENCE TO PRIOR APPLICATIONS

This application is the U.S. National Phase application under 35 U.S.C. § 371 of International Application No. PCT/EP2016/068794, filed on Aug. 5, 2016, which claims the benefit of European Patent Application No. EP15180180.0, filed on Aug. 7, 2015. These applications are hereby incorporated by reference herein.

FIELD OF THE INVENTION

The present invention relates to a device and system for monitoring an eye of a subject.

BACKGROUND OF THE INVENTION

One of the main responsibilities of an anesthesiologist or nurse anesthetist during a surgical procedure is the management of a patient's nociception level (i.e. pain) via the administration of analgesia (typically fast acting opioid analgesics, e.g., Remifentanil, Sufentanil, Fentanyl). Pain management is important for humanitarian reasons, to help in improving the efficacy of many general anesthetics and because of significant physiological benefits (cf. Stomberg M W, et al. Assessing pain response during general anesthesia, AANA Journal 2001, 69(3):218-222). This latter point is important, since although the patient is unconscious during the surgical procedure, they still experience a physiological 'stress' response to the nociceptive stimuli (e.g. surgical incision, intubation) which involves activation of the body's vasomotor Sympathetic Nervous System (SNS) and inhibition of the cardiac Parasympathetic Nervous System (PNS).

In addition, pain management is also important in the post-operative period since it has implications for patient recovery and discharge from hospital (Pyati S, Gan T J., Perioperative pain management, CNS Drugs. 2007, 21(3): 185-211). Pain management is required since during surgery patients must not be in pain but over-dosing of analgesic agents must be avoided. In the post-operative period administration of too much pain drugs or too little has important implications for patient recovery and discharge from hospital. Despite the recognition of the importance of effective pain control, up to 70% of patients still complain of moderate to severe pain postoperatively. Pain management has also become increasingly important since pain level is a key indicator used to assess the quality of care delivered by a hospital. Despite the importance of pain management during the perioperative period, there are very few products that offer an objective method for the assessment of the pain (i.e. nociception) level and, by extension, depth of analgesia level of a patient, especially intra- and post-operatively. These products mainly focus on how vital signs react to nociceptive stimuli. Pain management is also of great importance to intensive care units (ICU), neonatal intensive care units and patients in the general ward and at home who could experience periods of pain.

One approach to the monitoring of sedated patients includes the anesthesiologist manually adjusting the analgesia depth (i.e. the drug administration) based on an observation of patient movement and changes in three key parameters in response to nociceptive stimuli: heart rate (HR), non-invasive systolic blood pressure (NISBP) and bispectral index (BIS), which is an indicator of the sedation or hypnosis level as illustrated in FIG. 3. The anesthesiologist also observes patient reactions, like sweating, eye twitching and slight movements. Any of these could indicate inadequate analgesia.

Presently, in the operating room (OR), an anesthesiologist usually observes patient movement and changes in parameters like the heart rate, the blood pressure etc. for monitoring the pain level of a patient and for adjusting the analgesia depth. Also the blood Pressure, pulse Rate, Sweating, Tears (PSRT) algorithm as illustrated in FIG. 4 is widely used to monitor the pain level and depth of analgesia. The drawbacks of both of these approaches are that they are highly subjective, rely heavily on the experience of the clinician and are reactive to changes in patient condition, rather than being pre-emptive or predictive.

The drawbacks of both of these approaches are that they are highly subjective, rely heavily on the experience of the clinician and are reactive to changes in patient condition, rather than being pre-emptive or predictive.

An approach for providing an objective measurement is pupillometry. Traditionally, the healthcare professional observes the pupil size with the naked eye. Alternatively, automated video-pupillometry involves camera observation of the eye and automatic image analysis to segment out the iris, followed by determination of pupil diameter and, if needed, the quantification of the effect of a stimulus in percent. Video-pupillometry is the preferred method for scientific research and analysis of drowsiness. This, however, requires direct video access. Therefore, it cannot be performed continuously (i.e., it provides only a point measurement) and is unsuitable for use during surgery (eyes of the patient are taped shut to prevent drying out and corneal abrasion); sleep (closed eyes and movement) and use during the day (movement).

Although pupillometry is an established diagnostic approach to assess pain and brain function, a use in the OR during general anesthesia of a patient has so far been limited. One reason for this is that current pupillometry devices do not allow performing pupillometry if the eyes of the patient are closed. During prolonged general anesthesia this is, however, usually the case. For instance, visual access to the eye is not available during an operation generally since the eyes are taped shut and/or cream is applied to prevent dehydration of the eyes. Also, pupillometry is usually a hands-on activity (which would require an additional person in the OR) to hold the device and open up the eyes. Therefore, pupillometry is mostly used in the form of a spot-check measurement to determine a current state of the patient. Furthermore, excessive use of wires and devices touching the patient may decrease freedom of action for the surgery team. Current devices are often cumbersome and bulky and not very practical for an OR environment. Further, often additional components for preventing dehydration of the eye are required.

Another monitoring approach is based on pupillometry, which involves the measurement of pupil dilation, oscillations in pupil size, and pupillary light reflex amplitude (i.e. the difference between pupil dilation before and after light stimulation). A drawback of this method is that it cannot be performed continuously (i.e. it provides only a point measurement) and therefore is unsuitable for use during surgery. Another drawback of the use of pupillometry is that the eyes of a patient are typically taped shut during surgery to prevent them from drying out and avoid corneal abrasion.

In US 2014/0185010 A1 a method of monitoring the pupil of a subject is disclosed. A sensor for observing the pupil is arranged between the cornea and the eyelid covering the cornea, the sensor is powered through the eyelid, and the pupil-observation signals delivered by the sensor are collected through the eyelid.

There is, however, still a need for improving anesthesia and pain monitoring solutions for being applied during anesthesia, in particular with respect to accuracy and reliability.

SUMMARY OF THE INVENTION

It is an object of the present invention to provide a device for monitoring an eye of a subject and a corresponding monitoring system with an improved level of accuracy. In particular, it is an object of the present invention to provide a device that allows monitoring a pain level and/or a level of analgesia.

In a first aspect of the present invention a device for monitoring an eye of a subject is presented. The device comprises:

a transparent carrier for being in contact with the eye of the subject; and a photosensor facing the eye of the subject for receiving light reflected from the eye of the subject and for determining a light intensity of the received light, wherein the photosensor is arranged on the transparent carrier; and wherein the photosensor includes one of: a plurality of photodetectors arranged in the form of a two-dimensional array and spaced apart from one another for allowing incident light to pass between the photodetectors to enter the eye of the subject; and a single large area photodetector covering an iris and a pupil of the eye of the subject.

In another aspect, a system for monitoring a pain level of a subject is presented. The system comprises:

a device disclosed herein for being applied to an eye of the subject;

a communication interface for communicating with the device and for receiving from the device at least one of the light intensity and a monitoring parameter determined based on the light intensity; and a monitoring interface for providing information determined based on the received at least one of the light intensity and the monitoring parameter.

Preferred embodiments of the invention are defined in the dependent claims. It shall be understood that the claimed system has similar and/or identical preferred embodiments as the claimed device and as defined in the dependent claims.

The present invention is based on the idea of monitoring an eye of a patient and in particular the size and the position of a pupil in the eye (pupillometry). The behavior of the pupil, in particular, the size and the frequency, amplitude and speed of changes of the diameter of the pupil carry information on the patient. The device of the present invention allows monitoring the eye while the eye is open and/or while the eye is closed, i.e. while the eyelid is in front of the pupil or is not in front of the pupil.

To provide this monitoring, the device of the present invention includes a transparent carrier, which is in contact with the eye of the subject when the device is applied. This transparent carrier may particularly have the form of a contact lens. The transparent carrier allows the eyelid of the patient to be closed. The transparent carrier may be manufactured of a hard or soft material that can be applied directly to the eye of the subject. As used herein, transparent may also refer to semi-transparent in some embodiments.

On this transparent carrier a photosensor is arranged. The photosensor is arranged to face the eye of the subject and to receive light that is reflected from the eye of the subject. The photosensor may be glued to the transparent carrier or may be manufactured in a combined manufacturing process, i.e. be manufactured integrally with the transparent carrier. For instance, the at least one photodetector may be an organic photodetector that can be manufactured in a more or less arbitrary shape.

Independent of the eyelid of the subject being shut or open, light is reflected from the eye (in particular from the iris and the pupil). The reflected light can be captured by means of at least one photodetector in the photosensor. The pupil reflects less light than the iris and/or than the white of the eye. Thus, a size measure being indicative of the diameter of the pupil of the subject can be derived from the measured reflections. The bigger the pupil, the more light is absorbed and the less light is reflected. This size measure is indicative of different physiological measures of the subject and can form the basis for pupillometry.

In addition to at least one photodetector for detecting light, the photosensor further includes readout electronics for reading out the at least one photodetector and for determining a signal corresponding to a light intensity. The readout electronics comprises the wiring for connecting the plurality of photodetectors and the required peripheral electronics. The readout electronics may also provide limited signal processing capabilities. The readout electronics is usually arranged on the transparent carrier along with the at least one photodetector. Parts of the readout electronics may, however, also be separate from the carrier.

In an aspect, the photosensor includes a plurality of photodetectors arranged in the form of a two-dimensional array and spaced apart from one another for allowing incident light to pass between the photodetectors to enter the eye of the subject. This arrangement allows incident light to enter the eye in spite of the photodetectors being able to provide a two-dimensional distribution of the reflected light. The signals of the plurality of photodetectors form a two-dimensional light intensity distribution being indicative of the amount of light captured or reflected, respectively, at different locations on the eye. The light intensity determined by the photosensor corresponds to a two-dimensional light intensity distribution. This two-dimensional light intensity distribution forms the basis for deriving therefrom a diameter of the pupil and its development over the time. Preferably, each photodetector of the plurality of photodetectors provides a binary signal indicating whether or not it captures light. Such a value may, e.g. be determined based on a predefined threshold or based on a threshold being determined in a calibration procedure or a relative threshold. The light intensity or the two-dimensional light intensity distribution then corresponds to a matrix of binary values. The binary signal indicates whether the photodetector is located over the pupil and captures only a small amount of light or over the iris or white of the eye and captures more light since more light is reflected therefrom. By evaluating the two-dimensional light intensity distribution it becomes possible to obtain an accurate measurement of the pupil size.

In another aspect, the photosensor includes a single large area photodetector covering the iris and the pupil of the eye of the subject. The single large area photodetector may be bigger than the pupil and the iris, i.e. cover a larger area. The single large area photodetector may correspond to sort of one-pixel photodetector. In comparison to the use of a plurality of photodetectors, the single large area photodetector provides only one single signal indicating a total intensity of the captured light. This signal then corresponds to the light intensity. However, the light intensity is still proportional to the pupil size since a bigger pupil will result in less light being reflected.

The device of the present invention may be integrated into a monitoring system. The device may then provide the measured light intensity or a parameter being derived therefrom to an external communication interface which is in communication with a monitoring interface. The monitoring interface, e.g. in the form of a computer screen or the like, may then provide the data of the device or a parameter being determined based thereupon to a physician or other medical personnel. For instance, a person in an operating room (OR) or an intensive care unit (ICU) may obtain information on a pain level or analgesia level of the patient being currently treated.

In comparison to previous approaches both the use of a plurality of photodetectors and the use of the single large area photodetector as described above allow providing a higher measurement accuracy with respect to a pupil size being determined based on the light intensity. A light intensity measurement provided by the device of the present invention results in higher reliability and significance of pupillometry measurements derived therefrom.

In principle, it would also be possible to provide a monitoring based on a single row of photodetectors or based on a matrix detector being small in comparison to the eye. A light distribution provided thereby, would, however, be less reliable and less significant with respect to any parameter determined based thereupon.

A matrix detector necessarily has to be small in comparison to the eye, i.e. not cover the iris and the pupil of the eye, since incident light has to enter the eye at its sides. Making use of a larger matrix detector would result in less light entering the pupil and being reflected. Thus, it would not be possible to provide a measurement when the eyelid is closed (and only a small amount of light can enter the eye). The use of a comparatively small matrix detector, however, results in an inaccurate measurement since the covered area can only be small. Alternatively, an additional light source might be used, which would, however, result in an increased complexity and higher costs.

Furthermore, the position of the transparent carrier with respect to the eye is usually not fixed. In other words, the transparent carrier may move relative to the pupil, iris and white of the eye. Thus, the plurality of photodetectors arranged on the transparent carrier is also not always in the same position with respect to the eye and the pupil of the patient. A measurement provided by a single row of photodetectors cannot detect such movement. In contrast thereto, a two-dimensional array of photodetectors allows providing an accurate size measurement and distinguishing between the pupil moving and the pupil changing its diameter.

The arrangement of the photodetectors according to the present invention allows ensuring full coverage of the pupil. Both the use of the two-dimensional array with photodetectors being spaced apart from one another and the use of the single large area detector allow covering a comparably large area. Thereby, not only erroneous measurements if the pupil slipped out of the detector matrix are prevented, but also a better resolution that enables tracking pupil (micro-) oscillations can be obtained.

In comparison to previous pupillometry monitoring approaches based on devices that are to be applied externally to the eye of the subject, the present invention can also be applied while the eyelid of the subject is closed. This makes it possible to monitor the eye of the subject during a medical operation when the patient is under anesthesia. Furthermore, the present invention does not inhibit freedom of action in any way since it allows a completely wireless operation. No changes of the workflow in an OR setup are required. The necessary preparations such as applying the transparent carrier to the eye of the patient and performing an initial functionality check can be done during the prep time.

In a preferred embodiment the photosensor includes the plurality of photodetectors; and the plurality of photodetectors is arranged in a plurality of rows of photodetectors, in particular at least three parallel rows, or in a plurality of concentric circles substantially covering the iris and the pupil of the eye of the subject. The plurality of rows or concentric circles is spaced apart from one another. Advantageously, the rows may extend at least from one side of the pupil to the other side of the pupil. Thereby, the determined light intensity, i.e. the two-dimensional light intensity distribution, allows deriving an accurate measure for the pupil diameter. Further, by arranging the photodetectors in at least three parallel rows, it also becomes possible to accurately cope with movements of the pupil relative to the transparent carrier. For instance it may be assumed that the central point of the pupil of the subject is aligned with the central of the three parallel rows. Then, a move of the pupil relative to the transparent carrier and to the at least three parallel rows can be detected by evaluating the corresponding portions of the two-dimensional light intensity distribution generated based on the signals of the photodetectors. Additionally, such a configuration allows for pupillometry on irregular shaped pupils, which would be very hard to do with a single line of photo detectors.

In another preferred embodiment the photosensor includes the single large area photodetector; and the single large area photodetector includes a transparent photosensitive material, in particular Indium Tin Oxide, ITO, for passing incident light into the eye of the subject. Thus, the single large area photodetector is preferably made of a transparent material allowing incident light to enter the eye of the subject through the photosensor. Thereby, the amount of light that reaches the eye and that is reflected at the eye for being captured at the photosensor is increased. This allows for a more accurate measurement.

In an embodiment the transparent carrier includes a filter for passing light of a predefined wavelength and/or the photosensor is configured to detect light of the predefined wavelength. In other words, a filter may either be included in the transparent carrier or in the photosensor itself. Such a filter may allow filtering the incident light and exploiting properties of light of a distinct wavelength. For instance, by filtering the incident light effects resulting from fluctuations of the ambient light in a certain portion of the spectrum may be compensated.

Preferably, the predefined wavelength corresponds to the isosbestic point of light absorption of oxygenated hemoglobin and deoxyhemoglobin in the blood of the subject or is predetermined based on the color of the eye of the subject. The blood of the subject circulating in the eyelid of the subject influences the incident light. In particular, oxygenated hemoglobin and deoxyhemoglobin have a wavelength-dependent light absorption characteristic. Thus, different amounts of light are absorbed depending on the current blood-oxygen-saturation of the subject. This influences the determined light intensity. In particular, the light intensity may vary due to this effect at certain locations (in the vicinity of blood vessels). Thereby, assessing the size of the pupil of the subject based on the light intensity or any other further processing may become inaccurate. The light absorption of hemoglobin and deoxyhemoglobin are equivalent at the isosbestic point. Thus, filtering the incident light based on this wavelength (i.e. the wavelength corresponding to said isosbestic point) allows compensating this effect. In another embodiment, the predefined wavelength may also be predetermined based on an eye color of the subject. Depending on the eye color, i.e. the color of the iris, light is reflected differently. In particular, different wavelengths are more or less reflected. Thus, making use of a dedicated wavelength determined based thereupon allows optimizing the measurement. This allows providing accurate measurements for patients with different eye colors. In other words, the device of the present invention may be optimized for detecting light of a wavelength being determined based on the eye color of the subject. Thereby, the contrast between the pupil and the iris of the eye of the subject is optimized.

In a preferred embodiment the device further comprises a processor for determining a pupil parameter being indicative of a size of a pupil of the subject based on the determined light intensity. The processor processes the light intensity. For instance, in case of a light intensity corresponding to a two-dimensional light intensity distribution including binary values depending on whether or not the respective one of the plurality of photodetectors is over the pupil or not, the processor may carry out edge detection algorithms or other image processing algorithms for deriving regions in the two-dimensional light intensity distribution representing the pupil and/or the iris of the eye of the subject. In case of a single large area photodetector the processing may be simpler but may possibly be carried out at a higher frequency, since only a single signal has to be processed. In particular, the size of the pupil and its development over time are of interest and form the basis for pupillometry approaches. It is possible that the processor is arranged on the transparent carrier. It is also possible that the processor is arranged externally.

Preferably, the processor is configured to determine at least one of a pain parameter being indicative of a pain level of the subject and/or an analgesia parameter being indicative of a depth of analgesia of the subject based on the pupil parameter. By analyzing the development of the size of the pupil and its changes over time it becomes possible to derive therefrom a parameter being indicative of a pain level and/or a depth of analgesia of the subject. For instance, the pupil of a subject suffering from pain may show a higher frequency of size changes. The pupil changes its size in response to pain stimuli. Furthermore, the pupil will not show a high level of activity while the subject is under anesthesia and analgesia. Both parameters may be determined by evaluating the pupil size of the subject and its development over time and may be used by medical personnel, e.g. for adjusting a drug level during an operation.

Furthermore, it is possible that the processor is configured to determine the pain parameter and/or the analgesia parameter further based on a vital sign of the patient and/or based on a second pupil parameter being indicative of a size of the second pupil of the subject. By additionally considering a vital sign of a patient it becomes possible to derive the pain parameter and/or the analgesia parameter with a higher accuracy, i.e. with a higher significance. For instance, the heart rate, the blood pressure, the breathing rate or further vital signs may be considered. Such vital signs may be measured by means of other devices, such as a heart rate monitor etc. Additionally, a second pupil parameter can be considered being indicative of a size of the second pupil of the subject. Thereby, it becomes possible to obtain a pain parameter and/or an analgesia parameter with a higher significance. Also, it may become possible to compensate for effects that occur for one eye only. For instance, one eye may be subject to external light influences disturbing the measurement. This may be compensated by additionally evaluating the second eye of the subject. The accuracy is increased. In particular, it may be possible that both eyes of the subject are monitored by means of a device as described above and the determined light intensities for both eyes may be evaluated in a processor in one of the two transparent carriers being in contact with the two eyes of the subject or in a two processors being in communication with one another.

In an embodiment the device further comprises a second photosensor facing away from the eye of the subject for receiving incident light and for determining a light intensity of incident light. If additionally a measurement of the incident light, i.e. the external light entering the eye prior to being reflected, is available it becomes possible to compensate for disturbances caused by ambient light. Such disturbances may result from flickering light being caused by an external light source or by a movement of the subject's head, e.g. by looking out of the window etc. The processor may be configured to include this additional measurement when processing the pupil parameter. Thereby, it may be possible that a second photosensor is included in the device. It may, however, also be possible that the second photosensor corresponds to a photosensor integrated with the first photosensor. For instance, in an embodiment in which the photosensor includes rows of photodetectors, it may be possible that every second row of photodetectors faces away from the eye of the subject, i.e. in the direction of the incident light. Then, it becomes possible to accurately compensate different and varying disturbances caused by incident light affecting the different photodetectors facing the eye of the subject. The signal provided by the second photosensor will preferably also be provided to the processor, e.g., for being considered in the processing of the pupil parameter.

In another embodiment the transparent carrier includes at least one of: a power storage unit, in particular a thin-film battery, for enabling a self-sufficient operation of the device; and a power interface for receiving electrical power, in particular a wireless power interface for receiving power wirelessly. A power storage unit may be represented by any form of battery arranged on the transparent carrier. By making use of a battery, it becomes possible to construct a completely self-sufficient device that does not require to be connected to the outside. For instance, if the device is used during an operation of the subject, it may not be possible to make use of a wired connection. The use of a thin-film battery allows obtaining a small and thin device that may still be arranged under the eyelid of the subject. As an alternative or in addition to making use of the power storage unit it may also be possible to receive electrical power wirelessly via a power interface. This power interface may, e.g., function inductively or electromagnetically. Usually, a corresponding power transmission interface is required external to the eye of the subject that is connected to mains power and that allows transmitting power to the power interface in the device. If a power interface is used in addition to a battery, it becomes possible to reduce the capacity of the battery and to allow for a comparably long-term operation of the device. For instance, it may be required that the device operates for a few hours or longer time periods depending on the application scenario.

In another embodiment an electrical current output of the photosensor is used for powering the device. The light received by the photosensor results in a photocurrent which can also be exploited for powering the device. This represents a form of energy harvesting. Advantages include that the device can be powered without a further power interface and/or that the size of a battery can be reduced.

In yet another embodiment the transparent carrier further includes illumination means for emitting light into the eye of the subject. The illumination means illuminates the eye of the subject. Thus, in addition to any external ambient light, also the light emitted by the illumination means is reflected at the eye of the subject and can be captured by the photosensor. This results in more light being available than if the ambient light alone is used. The illumination means may, e.g., be represented by at least one of a light emitting diode, LED, an organic LED, OLED, an array of LEDs, an array of OLEDs and a waveguiding slab together with a lightguide for injecting light into the waveguiding slab. Preferably, the illumination means covers an iris and a pupil of the eye of the subject. Thereby, the provided illumination is as uniform as possible. This can, e.g. be obtained by making use of an array of LEDs or organic LEDs. Also, it may be possible that the transparent carrier itself is used as a waveguiding slab. Light might be coupled into the transparent carrier from one side by means of a lightguide and the transparent carrier may be designed to emit the light in the direction of the eye. In this case no further components are required. A waveguiding slab refers to a light-guiding component. The illumination means may be used to trigger a pupillary response of the subject. Thereby, it becomes possible to trigger a reaction of the pupil of the subject which can be measured to derive therefrom information, e.g. on the pain level or depth of analgesia of the subject. It may also be possible to make use of the illumination means in a calibration procedure.

In an embodiment the illumination means is configured to emit light at the isosbestic point of light absorption of oxygenated hemoglobin and deoxyhemoglobin in the blood of the subject; at the isosbestic point and at another wavelength alternatingly; or at a wavelength in the visible spectrum and at a wavelength in the infrared or near infrared spectrum alternatingly. An illumination means may be suitable for emitting light at a single wavelength, i.e. light of one particular color. Thereby, it becomes possible to reduce the device's susceptibility to external effects. For instance, the blood in the eye of a patient may have a varying level of oxygenated hemoglobin and deoxyhemoglobin. The absorption characteristics vary depending on this level. Thus, if an illumination means is used that emits light into the eye of the subject that a varying fraction of this light is absorbed. To compensate effects resulting therefrom, it is possible to emit light at the isosbestic point at which the absorption of light in the subject's blood is equal independent of the current level of oxygenation. Alternatively or additionally this behavior may also be exploited. For instance, it is possible to derive a heart rate, a breathing rate or a blood-oxygen-saturation from the measurement of this light absorption of the blood. Thus, if light at a wavelength other than the isosbestic point of light absorption is emitted through or is reflected in the corresponding tissue layer, e.g. in the eye or the eyelid, it is possible to monitor this fluctuation. Thus, the one or more photodetectors in the device of the present invention can also be used to obtain information being indicative of one of these vital signs. For this, it may be advantageous to operate the illumination means to emit light at the isosbestic point of light absorption and at another wavelength alternatingly to obtain a vital sign measure and an adequate two-dimensional light intensity distribution forming the basis for pupillometry processing alternatingly.

In yet another preferred embodiment the transparent carrier includes a shielding layer for blocking incident light from entering the eye of the subject. The shielding layer will usually be arranged on a side of the transparent carrier facing away from the eye of the subject. The shielding layer may correspond to a layer of non-translucent material to prevent incident light from entering the eye of the subject. Only light from the illumination means is then reflected at the eye. This light may be controlled with respect to a color or illumination frequency. Thus, it becomes possible to provide controlled measurement conditions. The light intensity as captured by the photosensor is less influenced by ambient light effects. Thereby, the obtained light intensity better represents the actual pupil size. Also, the sensitivity of the one or more photodetectors towards the eye, i.e. in the direction of the pupil and the iris of the subject may be increased. In an embodiment the shielding layer may also be integrated with a photodetector in the form of a layer of non-translucent material deposited at the side of the photodetector facing away from the eye. Thus, an individual photodetector has an individual shielding layer.

In yet another embodiment, the processor is configured to determine a calibration parameter for the subject by determining a pupil diameter of the pupil in a normal state and in a stimulated state. The pupil reacts to stimuli. This may be exploited by stimulating the pupil and measuring the light intensity directly after the stimulation. By performing a calibration, it becomes possible to obtain a measurement of the pupil size that also considers possible differences among different subjects. The calibration is performed for a particular subject. Thus, the measurement becomes individualized to a certain degree.

In another embodiment the device further comprises an external light source, in particular a laser and/or a light emitting diode, LED, for emitting light into the eye of the subject. The external light source is used for emitting light into the eye of the subject to be reflected and captured by the photosensor. In comparison to the above-described illumination means on the transparent carrier the external light source is, however, arranged externally to the eye of the subject. The functions of the external light source are comparable to the functions of the illumination means. With respect to calibration, an external light source may be used to trigger a pupillary response of the subject. Also, if a photosensor including multiple photodetectors is used and the external light source corresponds to a laser emitting small light bundles is used it becomes possible to direct one of these light bundles to one single photodetector for calibration. In an embodiment the external light source is configured to emit light at the isosbestic point of light absorption of oxygenated hemoglobin and deoxyhemoglobin in the blood of the subject; at the isosbestic point and at another wavelength alternatingly; or at a wavelength in the visible spectrum and at a wavelength in the infrared or near infrared spectrum alternatingly. Thereby, it becomes possible to exploit the above-described effect with respect to the blood-oxygen-saturation. The external light source emits light that may pass through the eyelid prior to being reflected. Thus, the influence of blood in the eyelid may add to the influence of blood in the eye.

In yet another embodiment the device further comprises a communication interface, in particular a wireless interface, for communicating with an external processing and/or display device. This communication interface is used for communicating with an external device that may provide the determined information to medical personnel. For instance, an anesthetist may be provided with the determined pain parameter or analgesia parameter for obtaining therefrom information on how to further administer a drug to a patient during an operation. Depending on the transmitted information it may also be possible to perform the processing partly or entirely by means of an external processing device. For instance, the two-dimensional light intensity distribution may be communicated to the external device to perform all further processing thereon.

In further embodiments it may also be possible that the processor is configured to determine a vital sign of the patient based on the two-dimensional light intensity distribution. In yet another embodiment it may also be possible that the system further comprises a drug dispenser for dispensing a drug to the subject in dependence of the determined pain parameter.

In an alternative, it is also possible that the device for monitoring an eye of a subject comprises a photosensor facing the eye of the subject for receiving light reflected from the eye of the subject and for determining a light intensity of the received light; and an external light source, in particular a laser and/or a light emitting diode, LED, for emitting light into the eye of the subject, wherein the photosensor is arranged in an on-eyelid housing for being applied to the eyelid of the subject, wherein the photosensor includes a single large area photodetector covering an iris and a pupil of the eye of the subject. Thus, it is also possible to make use of an on-eyelid device for being applied to an eye of the subject in combination with a single large area photodetector and an external light source.

In an alternative, a device for monitoring an eye of a subject comprises: a transparent carrier for being in contact with the eye of the subject; and a photosensor facing the eye of the subject for receiving light reflected from the eye of the subject and for determining a light intensity of the received light, wherein the photosensor is arranged on the transparent carrier; wherein the transparent carrier includes illumination means for emitting light into the eye of the subject; and wherein the transparent carrier includes a shielding layer for blocking incident light from entering the eye of the subject.

In an alternative a device for monitoring an eye of a subject comprises: a transparent carrier for being in contact with the eye of the subject; and a photosensor facing the eye of the subject for receiving light reflected from the eye of the subject and for determining a light intensity of the received light, wherein the transparent carrier includes illumination means for emitting light into the eye of the subject; and wherein the photosensor is arranged in an on-eyelid housing for being applied to the eyelid of the subject.

In another aspect, there is provided a method for monioring an eye of a subject, the method comprising the steps of a) receiving light reflected from the eye of the subject by means of a photosensor including one of: i) s plurality of photodetectors arranged in the form of a two-dimensional array and spaced apart from one another for allowing incident light to pass between the to enter the eye of the subject, wherein the plurality of photodetectors is arranged in a plurality of rows of photodetectors or in a plurality of concentric circles substantially covering the iris and the pupil of the eye of the subject; and ii) a single large area photodetector covering an iris and a pupil of the eye of the subject; b) determining a light intensity of the reived light; and c) determining a pupil parameter being indicative of a size of a pupil of the subject based on the determined light intensity. The method according to the present invention comprises analogous advantages as hereinabove elucidated, namely regarding the possibility to monitor the size of the pupil and its development over time thereby enabling robust and accurate pupillometry approaches.

In a preferred embodiment, the method further comprise the step of determining at least one of a pain parameter being indicative of a pain level of the subject and/or an analgesia parameter being indicative of a depth of analgesia of the subject based on the pupil parameter. This method enables the monitoring of the development of the size of the pupil and its changes over time, therefore enabling therefrom a parameter being indicative of a pain level and/or a depth of analgesia of the subject. For instance, the pupil of a subject suffering from pain may show a higher frequency of size changes. The pupil changes its size in response to pain stimuli.

In a yet other aspect, there is provided a computer program product comprising a computer readable medium having computer readable code embodied therein, the computer readable code being configured such that, on execution by a suitable computer or processor, the computer or processor is caused to perform any steps of the method described above. In particular, the computer readable code can be configured to cause the computer or processor to determine a pupil parameter being indicative of a size of a pupil of the subject based on the determined light intensity.

Additionally, the the computer readable code can be configured to cause the computer or processor to determine at least one of a pain parameter being indicative of a pain level of the subject and/or an analgesia parameter being indicative of a depth of analgesia of the subject based on the pupil parameter.

BRIEF DESCRIPTION OF THE DRAWINGS

These and other aspects of the invention will be apparent from and elucidated with reference to the embodiment(s) described hereinafter. In the following drawings FIG. 1 schematically illustrates different embodiments of devices according to aspects of the invention;

FIG. 4 illustrates the PSRT (blood Pressure, pulse Rate, Sweating, Tears) scoring algorithm;

FIG. 5 schematically illustrates a device including a photosensor with a plurality of photodetectors according to an aspect of the present invention in side view and in top or frontal view;

DETAILED DESCRIPTION OF THE INVENTION

Figure 2:
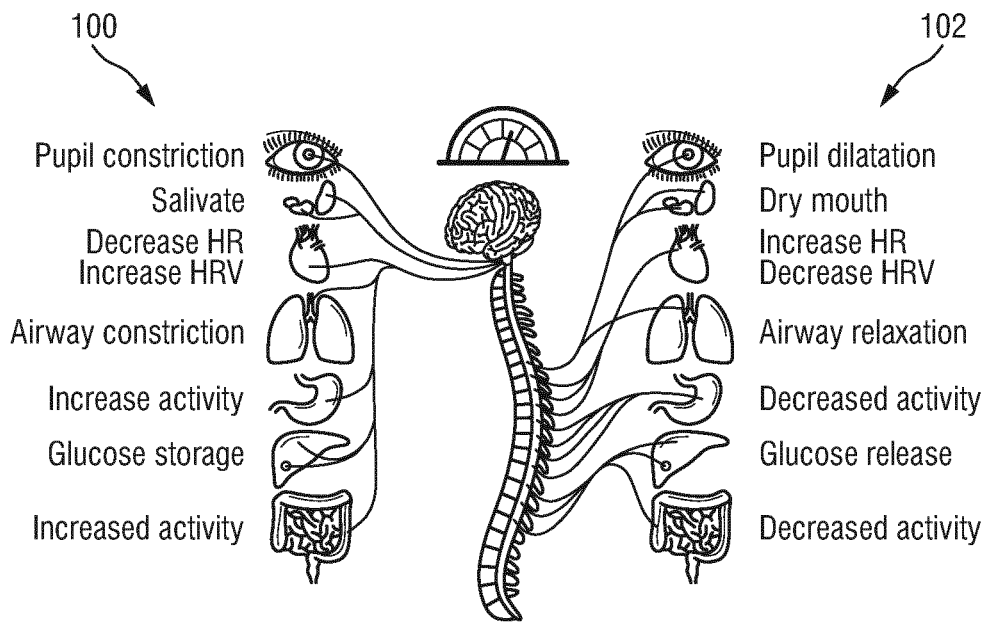
FIG. 2 illustrates the different physiological responses of the parasympathetic and sympathetic nervous systems.
Figure 3:
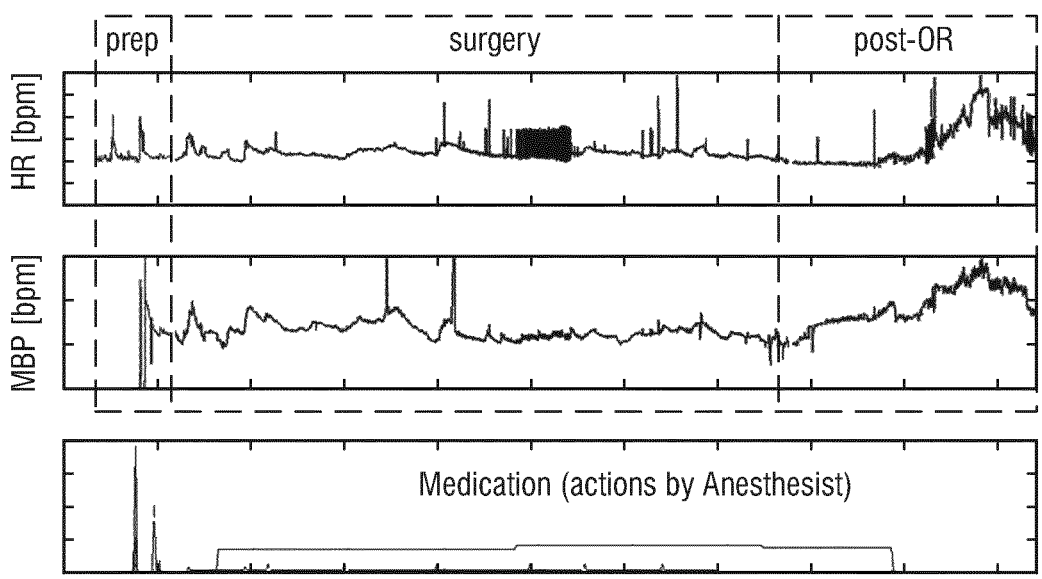
FIG. 3 illustrates an approach to monitor a depth of analgesia during an operation.

The present invention aims at providing an approach to accurate pain and/or depth of analgesia monitoring. A device according to the present invention may particularly be put to use during an operation for providing information to an anesthetist. The device is based on the principle concept of capturing light that is reflected at an eye of a patient by means of a photosensor. There are essentially three different areas in the eye: a) the white of the eye, which will reflect the most light, b) the iris, which will absorb more of the light in comparison to the white and thus reflect less light, and which may result in the reflected light being changed in color due to the color of the iris and c) the pupil, which is essentially a hole in the iris and will reflect little to no light. The size of the pupil and the iris of the eye vary in response to pain and other stimuli. Such variations can be observed by capturing reflected light with a photosensor. Thus, the intensity of the reflected light carries information on the pupil size and on pain and other stimuli. Based thereupon, information on the state of the patient can be derived.

FIG. 1 schematically illustrates embodiments of devices 10a, 10b, 10c, and 10d according to aspects of the present invention that provide this functionality. In the following, the use of the reference numeral 10 indicates that all different aspects are referred to, i.e. that the described feature can be applied to all embodiments 10a, 10b, 10c, and 10d.

FIG. 1 shows a schematic sectional view of a device 10 applied to an eye 14. Incident light 16 enters an eye 14 of a subject and is reflected. An eyelid 18 of the eye may be closed. The reflected light is captured by a photosensor 20. The photosensor 20 faces in the direction of the eye 14. As illustrated, light can pass through or be absorbed by the pupil 28 whereas it is reflected at the iris 26 (and at the white of the eye) to a certain degree. The reflections can thus be used to determine pupil size.

In FIGS. 1a and 1b devices 10a, 10b according to aspects of the present invention are schematically illustrated. Incident light may enter the eye 14 through the eyelid 18. Both embodiments 10a, 10b comprise a transparent carrier 12 that is in contact with the eye 14 of the subject. On the transparent carrier 12 a photosensor 20 is arranged that allows capturing light reflected from the eye of the subject and determining a light intensity of the received reflected light. The photosensor 20 illustrated in FIG. 1a includes a plurality of photodetectors 22 arranged in the form of a two-dimensional array and spaced apart from one another for allowing incident light to pass between the photodetectors 22 to enter the eye 14 of the subject. The photosensor 20 illustrated in FIG. 1b includes a single large area photodetector 24 covering an iris 26 and a pupil 28 of the eye 16 of the subject.

In FIG. 1c another variation of a device according to an aspect of the present invention is schematically illustrated. The illustrated device 10c includes a transparent carrier 12 for being in contact with the eye 14 of the subject. Further, the device 10c includes a photosensor 20 facing the eye 14 of the subject. The photosensor 20 is arranged on the transparent carrier 12 and receives light that is reflected at the eye of the subject and determines a light intensity of the received light. The device 10c further includes illumination means 30 for emitting light into the eye of the subject. The illumination means 30 is arranged on the transparent carrier 12. Further, the device includes a shielding layer 32 which blocks incident light from the ambience from entering the eye 14 of the subject. As illustrated in FIG. 1c the photosensor 20 may include a plurality of photodetectors 22. It is, however, also possible that the photosensor 20 includes a single large area photodetector (not illustrated).

In FIG. 1d another variation of a device according to an aspect of the present invention is schematically illustrated. The illustrated device 10d includes a transparent carrier 12 for being in contact with the eye 14 of the subject. Further, the device 10d includes a photosensor 20 facing the eye 14 of the subject. The transparent carrier 12 includes illumination means 30 for emitting light into the eye 14 of the subject. The illumination means 30 is arranged on the transparent carrier 12. The photosensor 20 is arranged in an on-eyelid housing 34 for being applied to the eyelid of the subject.

The present invention is based on the following insights. As illustrated in FIG. 2, the human Parasympathetic 100 and Sympathetic 102 Nervous System show a physiological 'stress' response to the nociceptive stimuli (e.g., surgical incision, intubation, etc.). This response may involve an activation of the body's vasomotor Sympathetic Nervous System (SNS) and inhibition of the cardiac Parasympathetic Nervous System (PNS).

The present invention provides an approach to monitoring an eye of the patient. A typical application scenario of a device according to the present invention could be in an OR: A patient is brought into the OR or prepared for surgery in a preparation area. The device of the present invention is applied to one of the eyes of the patient. An initial measurement series is done to check whether a signal is produced and pupil size is measured. Then, the patient is asked to close his/her eyes to check functionality of the device with closed eyes. Afterwards, anesthesia is induced, and the eyes are closed and taped to prevent opening. During induction and maintenance of anesthesia the anesthesiologist obtains information on the pain level and/or on the depth of analgesia determined based on the light intensity provided by the device. Additionally, personal observations, vital signs and outputs of other devices may be taken into account to adjust the dose of anesthesia, analgesia and muscle relaxant agents to maintain an optimum patient state. After cessation of anesthesia, the device is removed. Alternatively, the device is retained to continue monitoring the patient during recovery in the post-operative period.

For instance, the device of the present invention may be used to provide an anesthesiologist with a pupil parameter such as an inferred pupil size in real-time, a current pupil diameter, a moving average and/or minimum and maximum numbers of the pupil diameter over the last 10 s (or another set amount of time), a number showing a pupil oscillation frequency and/or minimum and maximum numbers over the last 10 s (or another set amount of time), pupillary microoscillations, the pupillary reflex to a light or pain stimulus, or a combination of two or more of the above. Furthermore, it may also be possible that the anesthesiologist is provided with a pain or analgesia parameter, e.g. determined based on a pupil parameter. Such a parameter may indicate a depth of analgesia, anesthesia and/or pain level and may be calculated by an algorithm taking into account baseline levels, trends and current values for pupil size and/or oscillation frequency. It may even be possible that one of the determined parameters is used in a closed-loop system to suggest or automatically alter the infusion rate or dose and dosing frequency of anesthesia and analgesia agents. Further, the anesthesiologist can be provided with an alarm when this parameter exceeds preset values indicating inadequate analgesia.

FIG. 5 schematically illustrates an embodiment of a device 10a according to an aspect of the present invention in sectional view (FIG. 5a) and in top or frontal view (FIG. 5b). Light is reflected at an eye 14 of a subject and a light intensity corresponding to a two-dimensional light intensity distribution (basically corresponding to an image of the eye) is obtained from the reflected light. In the illustrations herein the photodetectors and the number of photodetectors on a transparent carrier are not to scale.

The device 10a comprises a transparent carrier 12. The transparent carrier 12 may particularly have the form of a contact lens or comparable device. In a preferred embodiment the transparent carrier 12 corresponds to a contact lens. The transparent carrier 12 can be applied to the eye 14 of the subject. In particular, the transparent carrier 12 allows the eyelid (not illustrated) of the subject to be closed. The transparent carrier 12 is transparent in that it allows incident light to pass through it into the eye 12 of the subject.

The device 10a further comprises a photosensor 20 including a plurality of photodetectors 22 arranged on the transparent carrier 12. The photodetectors 22 face in the direction of the eye of the subject. The photodetectors 22 allow detecting light reflected at the eye of the subject. In particular, the photodetectors 22 may be represented by photodiodes, CCD pixels, CMOS pixels, organic photodetectors, etc. For instance, the transparent carrier 12 may comprise a series of photodiodes corresponding to the photodetectors 22 being placed in rows with spaces in between, so light can still travel through the transparent carrier 12 to reach the eye 14. At least one of the sides of the photodetectors 22 faces the eye of the subject. The photodetectors 22 are fixed to the transparent carrier 12, e.g. by means of glue. Also, it may be possible that the photodetectors and the transparent carrier are manufactured in a combined, i.e. integral, manufacturing process.

As illustrated in FIG. 5b the photodetectors 22 may, e.g., be arranged on the transparent carrier 12 in staggered rows of photodetectors 22 being spaced apart from one another in one dimension. The arrangement of the photodetectors with spaces in between them allows incident light to enter the eye and be reflected. Thus, an array of photodetectors can be used that assures an accurate measurement in spite of enough light entering the eye for performing the measurement also in low light conditions or with a closed eyelid.

Figure 6:
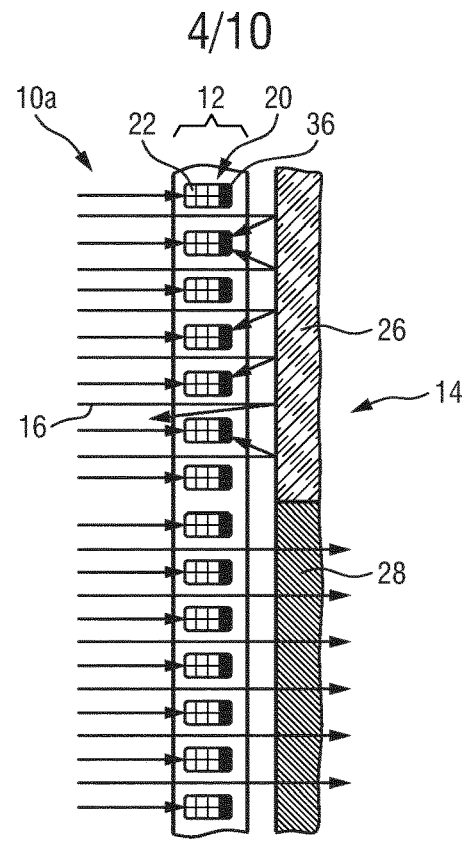
FIG. 6 schematically illustrates incident light passing through the transparent carrier and being reflected at the eye of the subject.

The device 10a is based on the idea that incident light is reflected at the eye. FIG. 6 illustrates the reflection schematically. Once the light reaches the eye 14, it is reflected. Reflectance by the eye 14 is accompanied by limited scattering, so that the reflected light is at an angle to the incident light 16, and can be detected by the photosensor 20 or, more precisely, by a photodetector 22 in the photosensor 20.

Incoming light 16 passes through the transparent carrier 12, is reflected by the iris 26 and white of the eye and detected by the photosensor 20. The reflected light is captured by the photosensor 20. Photodetectors 22 represented by photodiodes usually have higher sensitivity in one direction. This sensitive side 36 is facing towards the eye 14 of the subject for detecting reflected light. The photodetectors 22 covering the eye 14 will detect different levels and types (colors) of light based on the area of the eye 14 they cover. In particular, less light 16 is reflected at the pupil. Thus, the photodiodes covering the pupil 28 detect much less reflected light. This allows obtaining a contrast in the two-dimensional light intensity distribution that can be used to identify the three different areas and in particular to obtain a size measure for the pupil diameter for being used in pupillometry. The transition of the area with the highest reflectance (the white of the eye) to the intermediate area (the iris) can be used to identify the center of the pupil as the iris and the pupil are concentric. Thus, the size and the location (position) of the pupil can be tracked over time based on the two-dimensional light intensity distribution. For this, a threshold may be applied so that each photodetector in the plurality of photodetectors is attributed a binary value indicating whether or not it is located over the pupil or over the iris or the white of the eye.

Compared to previous approaches such as video pupillometry devices, an advantage of the device of the present invention is that pupillometry can be done with the eyes taped shut (i.e., closed eyes). Thus, continuous pupillometry during a surgical event or during sleep is possible. Further, the transparent carrier is always over the iris and pupil, so movement of the eye is compensated, also if eyes roll back/side during anesthesia. This ensures that the pupil is always in the field of view of the photosensor. This opens the way for continuous pupillometry with full freedom of movement for the user, e.g. during activities at home, work or possibly even sports.

Figure 7:
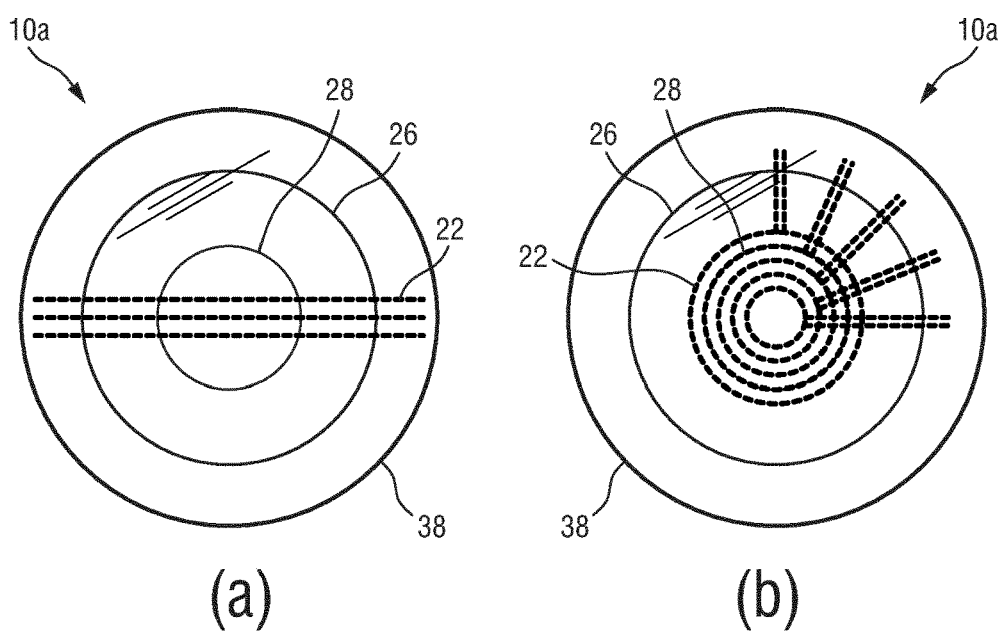
FIG. 7 schematically illustrates possible arrangements of a plurality of photodetectors on a transparent carrier in embodiments of the present invention.

FIG. 7 schematically illustrates two different possible two-dimensional arrays of photodetectors 22 according to embodiments of the present invention. The photodetectors 22 are arranged in a two-dimensional array on the transparent carrier 12. The photodetectors 22 are spaced apart from one another to allow incident light to travel through the spaces into the eye 14. The optimal size of the spaces between the photodetectors 22 may be determined based on the angle of scattering of light by the iris to capture as much of the reflected light as possible.

Preferably the photodetectors 22 cover the entire area of the iris 26 and pupil 28, i.e. are arranged in a two-dimensional array that is at least in one dimension larger than the iris 26. Thereby, an accurate measurement can be provided in spite of the eye 14 of the subject moving relative to the transparent carrier 12. It may be possible that the transparent carrier 12 moves relative to the iris 26, pupil 28 and white 38 of the eye 14 of the subject, e.g. due to eye movements. The two-dimensional arrangement of the photodetectors of the present invention allows providing an accurate measurement in spite of such movements. It is possible that the whole iris and pupil are covered since a sufficient amount of incident light to allow a measurement may travel into the eye through the spaces between the photodetectors 22.

It is possible to make use of a full grid including staggered rows with every second row being empty being placed over the complete transparent carrier as illustrated in FIG. 5b. Thereby, a large portion of the eye 14 is covered and the exact location of the pupil is irrelevant as long as the iris and pupil are in the field of view of the array. This is advantageous since general anesthesia may induce strabismus. The design of a full grid requires that the signal from each of the one ore more photodetectors 22 is processed separately to form the two-dimensional light intensity distribution. Then, however, the pupil diameter can be determined wherever the pupil is in the field of view of the array. A full grid also allows monitoring the size of irregular shaped pupils.

Alternatively, as illustrated in FIG. 7*a*, the photodetectors 22 may be arranged in three rows, wherein every second row is empty. Also, a higher number of rows may be possible. The rows span the iris 26 and the pupil 28 of the eye 14. Incident light travels through the "empty" rows/spaces into the eye 14. As the eye usually has a distinct curve, movement of the transparent carrier 12 relative to the eye will be limited by a proper design of the transparent carrier, i.e. the contact lens. Therefore, a limited number of rows of photodetectors 22 may be enough to accurately assess the diameter of the pupil. If a minimum of three rows of photodetectors is used it becomes possible to select the row that detects the largest pupil diameter as the "correct" row. This means that only a fraction of the two-dimensional light intensity distribution needs to be processed so that a lower complexity is required. A (much) larger space between the rows is also possible. If there are only three rows the distance between the rows could be equal to several hundreds of rows.

As illustrated in FIG. 7*b*, the photodetectors 22 may also be arranged in a plurality of concentric circles corresponding to a two-dimensional array. Most of the time a transparent carrier in the form of a contact lens will be concentric with the eye and the pupil. Thus, each circle will either be placed over the white 38 of the eye, the iris 26 or the pupil 28. Spatial resolution will depend on the number of concentric circles. Advantages are that each circle only needs to include a limited number of individual photodiodes, and the detected light intensity over each circle can be summed up such that a single value is created. Thus, the use of comparably simple readout electronics and processing is sufficient.

In comparison to previous approaches, the arrangement of the photodetectors in a two-dimensional array and being spaced apart from one another has the advantage that the diffuse light coming through the thin eyelid tissue has enough intensity that the reflected light can be detected. Therefore, the device will also function in the environment of an OR when the eyes are taped shut (provided that a transparent tape is used for this purpose), or during sleep or in other applications in which a direct analysis of the eye a pupil itself are difficult.

If the size of the photodetectors is sufficiently small compared to the size of the pupil, an accurate measurement of a pupil size can be made. In the current state of the art photodiodes in the order of micrometers can be manufactured, whereas the pupil has a diameter between 1.5 mm (bright light) and 8 mm (dim light). Thus, even when accounting for the required space between the photodiodes, a highly accurate estimation of pupil size is possible. If the refresh rate of the photodiodes is sufficiently higher than the oscillations of the pupil, also pupil size oscillation frequency can be detected in real time. Current photodiodes provide refresh rates in the order of microseconds, whereas in the literature pupil oscillations are generally monitored on the order of video rates. Pupil micro-oscillations may be in the order of milliseconds and are therefore also detectable with these refresh rates.

Another advantage of the evaluation of a two-dimensional light distribution determined by means of a device according to the present invention is that relative light levels are used. Therefore, variations in the thickness of the eyelids, the presence of eyelashes and the tape that will vary the incident light intensity over the eye will not render the measurements impossible to analyze.

Figure 8:
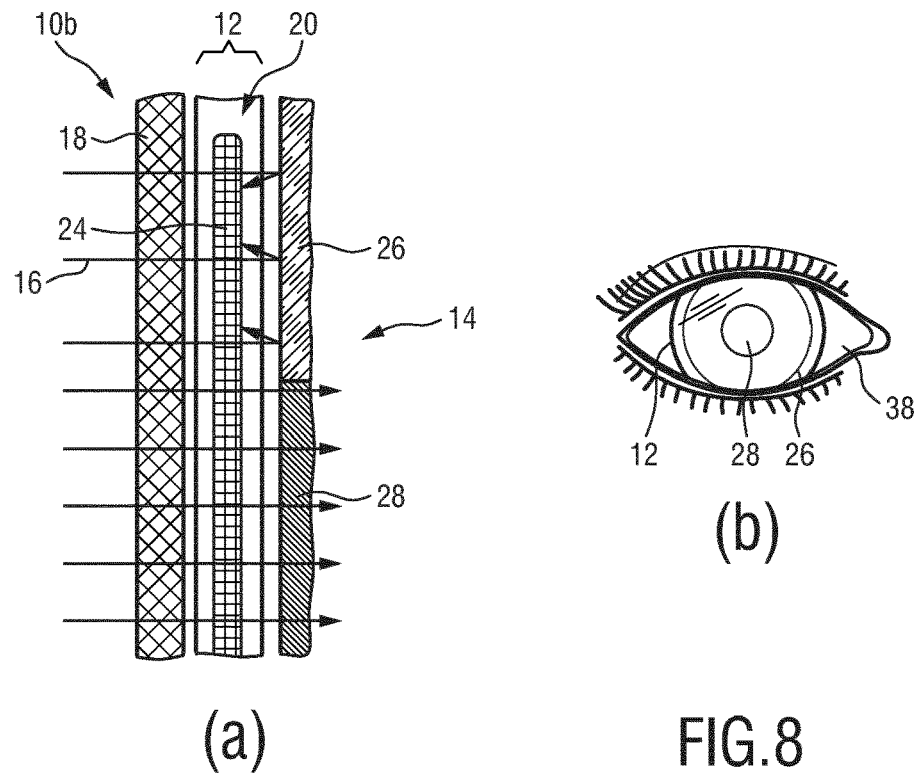
FIG. 8 schematically illustrates a device including a photosensor with a single large area photodetector according to an aspect of the present invention and its arrangement with respect to the eye of the subject.

In FIG. 8 another embodiment of a device 10*b* of the present invention (FIG. 8*a*) and its arrangement with respect to the eye of the subject (FIG. 8*b*) are schematically illustrated. It is to be understood that the above-described concepts and functionality can also be applied to this embodiment.

The above-described device 10*a*, in which the photosensor includes a large number of photodetectors that all require individual powering, read-out and communication of the value to an external device, may potentially require a comparably complex design and manufacturing. In the device 10*b* as illustrated in FIG. 8 a single large area photodetector 24 is used instead of the plurality of photodetectors. As briefly discussed with respect to FIG. 1*b*, the device 10*b* comprises a transparent carrier 12 on which a photosensor 20 is arranged. The photosensor 20 includes a single large area photodetector 24 covering the iris 26 and the pupil 28 of the eye 16 of the subject. Incident light 16 (ambient light or a dedicated external light source) travels through the eyelid 18 and through the transparent carrier 12 and is reflected at the eye 14. The device 10*b* and the single large area photodetector 24 records the total amount of reflected light by the eye, i.e. the light reflected by the iris 26 and possibly part of the light reflected by the white of the eye (depending on the size) and virtually no light reflected by the pupil 28. An increase in the diameter of the pupil 28 results in a lower total light reflection over the area covered by the photodetector 24 and therefore a lower level of signal (light intensity) and vice versa for a decrease in pupil diameter. This means that from the recorded light intensity, the diameter of the pupil can be derived. Thus, the device 10*b* requires only little complexity since only a single value per time point is required, only a single photodetector needs to be powered and only a single value needs to be read-out. This significantly simplifies the signal and data processing, the signal and data transmission, as well as the power consumption as multichannel communication and/or presence of local microprocessor (e.g. dedicated to communication) may not be necessary.

As illustrated in FIG. 8*b*, the device 10*b* basically consists of a transparent carrier 12 corresponding to a contact lens containing one single photodetector 24 preferably covering an area larger than the iris 26, i.e. partially covering the white 38 of the eye 14. The light intensity corresponding to the total reflected intensity can be correlated to the pupil area, since a larger pupil area will result in lower total reflected light intensity and vice versa. The total reflected light intensity is detected by the single large area photodetector unit as a single intensity value that corresponds to the sum of reflected light intensity from the sclera and iris. Since this is directly linked to the pupil size, it is possible to extract/calculate the pupil size information from the total reflected light intensity.

The use of the single large area photodetector allows obtaining a low-complexity device. Since the total reflected light intensity is measured with a single pixel detector, only one read-out value is created. This significantly simplifies the signal and data processing, signal and data transmission, as well as the power consumption as multichannel communication and/or presence of local microprocessor (e.g. dedicated to communication) are not necessary. The use of a single large scale photodetector may permit the use of simpler and cheaper components as the power and communication and spatial requirements (only one photodetector instead of hundreds to several ten thousands) are lower.

Preferably, the single large area photodetector and connectors (i.e. at least parts of the readout electronics) are manufactured with transparent photosensitive materials (e.g. ITO), so light can still travel through the contact lens to reach the eye. The photodetector may be an organic photodetector. Basically, all organic photo responsive devices (including organic solar cells) are capable of converting light into an electrical current. They can be manufactured by conventional solution processing methods like spin-on coating, ink jetting, dip coating, etc. Due to its polymeric nature, an organic photodetector is flexible to a certain extent (limited with the deformation that may result in damage/short circuit in charge carrying electrodes).

Furthermore, the pupil diameter typically varies between approximately 1.5 mm (bright light) and 8 mm (dim light). Often, the delta between consecutive measurements is more important than the absolute pupil size. Thus a high temporal resolution is desirable which is facilitated if only a single large area photodetector has to be read out. There are oscillations in pupil size at about 0.19-2.7 Hz. These, however, will usually not interfere and may even be quantified if the refresh rate of the photodetector is sufficiently higher than the oscillations of the pupil. Furthermore, the response to a pain stimulus becomes visible after a few seconds. State of the art photodetector refresh rates are in the order of microseconds. Thus, it is possible to measure the oscillations and pain responses. Also micro-oscillations may be feasible to measure with high enough refresh rates.

In an embodiment, it may also be possible to replace the single large area photodetector by rows of serially linked individual photodetectors. The advantage is similar, as still a single value is read-out and needs to be communicated. However, in this case staggered rows of photodetectors allow light to pass in between the rows. Therefore, the photodetectors do not need to be made of transparent materials.

Figure 9:
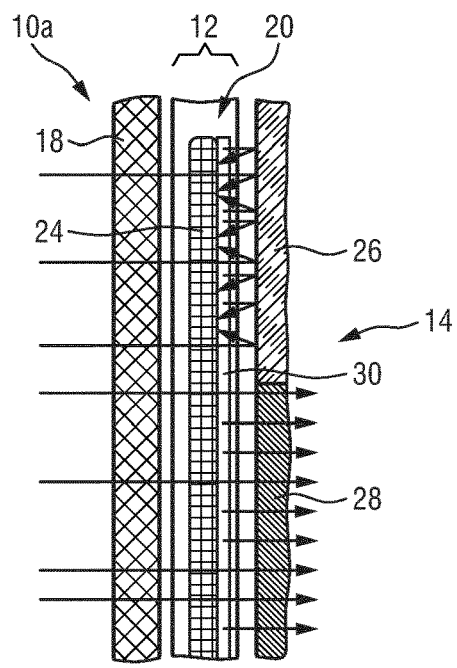
FIG. 9 schematically illustrates another embodiment of a device including a photosensor with a single large area photodetector.

In a preferred embodiment the device 10b may include illumination means 30 for increasing the amount of light that arrives at the eye 14 to reduce variations in incident light and to increase the resolution as illustrated in FIG. 9. The influence of the light transmission through the eyelid 18 is decreased. Thereby, the incident light intensity can be controlled, an improved spatial resolution due to minimized light scattering can be obtained, the susceptibility to blood flow induced variations over the eyelid can be reduced and a lower influence of skin color and/or eye lid thickness variations can be obtained.

Figure 10:
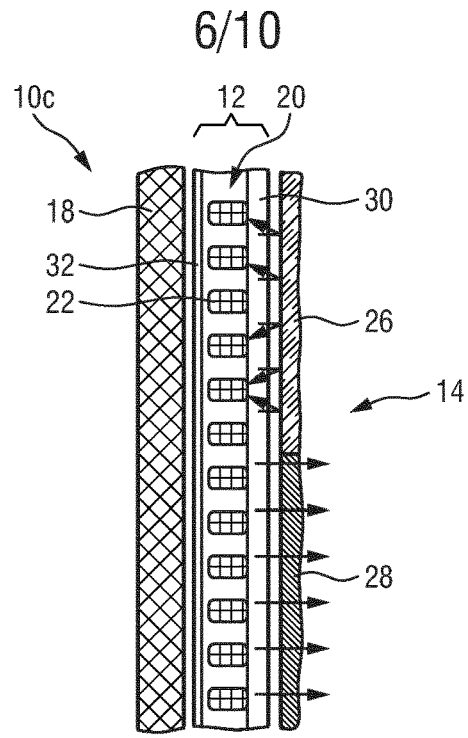
FIG. 10 schematically illustrates a device including illumination means and a shielding layer according to another aspect of the present invention.

In FIG. 10 another embodiment of a device 10c according to an aspect of the present invention is schematically illustrated. The device 10c comprises a transparent carrier 12 corresponding to a contact lens containing a shielding layer 32, illumination means 30 and a photosensor 20. The photosensor 20 preferably covers an area larger than the iris 26. Incident ambient light is blocked by the shielding layer 32 on the contact lens. The illumination means 30 generates light which reflects at the eye 14 at different intensities as described below. The sclera 38 reflects light at a maximum reflection intensity, the iris 26 reflects at an intermediate reflection intensity (depending on the iris color as well) and the pupil 28 reflects (almost) no light. The reflected light is detected by a photosensor 20 including an array of photodetectors 22, integrated between the shielding layer 32 and the illumination means 30 on the contact lens 12. From the signal of each individual photodetector, the pupil diameter can be calculated as outlined above.

The use of a shielding layer 32 is based on multiple considerations. Light may reach the photosensor via another way than via the eye. As a result, the detected light is not solely the reflected light from the sclera and iris. This creates a background value upon which a signal needs to be discerned. If the background value is not constant, this effect is worse. Further, the level of incident light may fluctuate due personal movement in the OR (shadow on the patient face), as well as movement of the head and of the eye of the wearer. Still further, the incident light has to cross the eyelids in applications with closed eyes. Thus, movement of the eyelid, variations in perfusion and oxygenation in the eyelid also increase noise and lower sensitivity of the measurement. Still further, if a photosensor including a single large area photodetector as described above is used, the total reflected light over the entire surface is used to calculate the pupil diameter. Thus, the influence of variations may be even stronger. The use of the shielding layer 32 thus results in that influences on the measurement from incident light such as an increased noise and/or a decreased sensitivity of the measurement can be avoided.

Embodiments of the device 10c may include data transmission/communication means, a data acquisition and processing device incorporated in the device or in a separate device (e.g. a computer, a computing unit or module that can be integrated into a patient monitor), signal and/or data receiver means, a program for analysis of the received data/signal, output means (e.g. a display) to inform the OR staff (e.g. anesthesiologist) of the patient status with respect to pain and consciousness and a processor for running algorithms, for example, to assess pain and consciousness levels based on the analyzed data.

Figure 11:
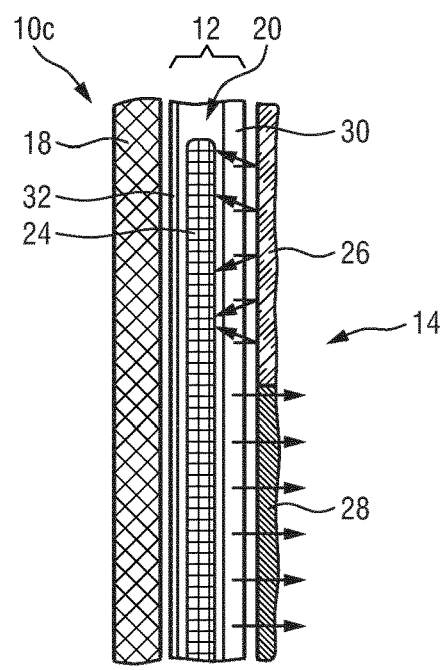
FIG. 11 schematically illustrates another embodiment of a device including illumination means and a shielding layer.

In the embodiment of the device 10c illustrated in FIG. 11, the photosensor 20 includes a single large area photodetector 24 as described above, in which the total amount of light reflected at the eye is recorded. A single large area photodetector is especially susceptible to variations in incident light, so that the beneficial effect of the decreased influence of incident light variations by using illumination means in combination with a shielding layer is high.

In an embodiment the illumination means and shielding may be combined with a photosensor in an on-eyelid housing for continuous pupillometry. On the one hand, the on-eyelid housing may be constructed of materials that block incident light, i.e. represent the shielding layer, or a shielding layer may be added to the non-eye side of the housing. On the other hand, the shielding layer may be included in the transparent carrier if the shielding is located together with the illumination means on an on-eye device, and the shielding is one-directional, i.e. blocks light moving towards the eye but not light coming from the side of the eye. As the shielding layer is in this case very close to the eye, ambient light from the side is blocked more efficiently than if the shielding layer is in the on-eyelid housing. The one-directional shielding on the contact lens usually only works if the illumination means is between the shielding and the eye (i.e. on the contact lens) otherwise there is no incident light and thus no reflection.

In an embodiment, the transparent carrier 12 may include a detector array and a shielding layer per photodetector. Next to adding a shielding layer to (a large part of) the device, small individual shielding layers may also be added to the individual photodetectors in a photodetector array. This way, ambient and/or external light may still cross the device to reach the eye in between the photodetectors, but can not reach the photodetectors directly. The advantage that the background signal in the photodetectors is minimized is retained, as only light reflected at the eye is detected by the photodetectors. Moreover, addition of an illumination means is not required in this embodiment. The advantage that variations in the incident light are prevented is lost.

Figure 12:
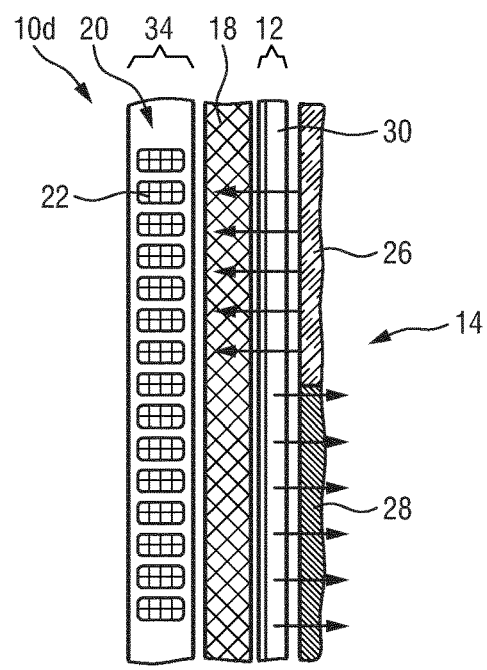
FIG. 12 schematically illustrates another embodiment of a device according to an aspect of the present invention wherein the photosensor is included in an on-eyelid housing.

In FIG. 12 another embodiment of a device 10d according to the present invention is illustrated, in which the photosensor 20 is integrated in an on-eyelid housing 34 for being in front of the eyelid 18. The device 10d includes illumination means 30 in a transparent carrier that is in contact with the eye 14. In the illustrated example, the photosensor 20 includes a plurality of photodetectors 22. As used herein the term on-eye device is used in contrast to on-eyelid housing and designates the components of the device 10d that are in direct contact with the eye, i.e. on the transparent carrier under the eyelid. The device 10d also allows for continuous pupillometry with closed eyes, opening the way for continuous pupillometry during a surgical event, or during sleep. An advantage of generating light by the illumination means on the transparent carrier is that the amount of incident light that arrives on the eye is increased with respect to ambient light and light from an external light source. Thus variations in incident light are minimized and the resolution is increased. Moreover, the level of incident light can more easily be controlled.

An on-eyelid housing 34 may correspond to any device for being worn on or in proximity to the eye of a person. The eye is fitted with a contact lens that contains a light source. The eyelids are closed and on top of the eyelids and an on-eyelid housing is placed that contains a series of photodetectors. Light generated by the illumination means is reflected at the eye. The reflected light travels through the transparent carrier and the eyelid and is detected by photosensor in the on-eyelid housing. The photodetectors in the photosensor in the on-eyelid device will detect different levels and types of light based on the area of the eye they cover. This provides a contrast that can be used to identify the three different areas of the eye. The info on detected light levels per photodetector (array) is sent to a computer. As the photodetectors are a 2D grid covering the eye (to a smaller or larger level, based on the location and number of photodetectors) the darker areas in the grid will represent the pupil. From this information the location and size of the pupil can be inferred, which can be used to track the size of the pupil in real time. The transition of the area with the highest reflectance (the white of the eye) to the intermediate area (the iris) can be used to identify the center of the pupil as the iris and the pupil are concentric.

The integration of a photosensor, in particular if it comprises a large number of photodetectors that all require individual powering, read-out and communication of the value to an external device, into the transparent carrier may lead to a highly complex device in design and manufacturing. This holds especially true when the spatial and emotional restrictions for a device that touches the eye are considered. Wired communication and powering of an on-eye device are challenging, whereas integrating local powering and wireless communication in a contact lens are equally or even more challenging. An on-eyelid housing, in which the photosensor is integrated, has the advantage of a simpler construction. Furthermore, triggering the pupillary light reflex usually requires a comparably high amount of light. The use of an on-eyelid housing in which the photosensor and the communication are included allows these deficiencies to be overcome. Thus, the main advantage is that the more complex functions of signal detection and communication are done in the on-eyelid device, which does not have the spatial restrictions of an on-eye device such as a contact lens. This increases the range of options for powering, communications and detection, allowing for less complex and costly solutions.

Embodiments of the device 10d comprise an illumination source, a power management subsystem that includes a power source and leads where necessary, communication means, an on-eyelid housing (e.g. a patch) comprising a photosensor, a power management subsystem, data transmission/communication means, a data acquisition and processing device that may be incorporated in the on-eyelid housing or in a separate device (e.g. a computer, a computing unit or module that can be integrated into a patient monitor), which includes signal and/or data receiver means, a program for analysis of the received data/signal, output means (e.g. display) to inform the OR staff (e.g. anesthesiologist) of the patient status with respect to pain and consciousness and optionally a processor for running algorithms, e.g., to assess pain and consciousness levels based on the analyzed data.

The device 10d may include illumination means in the transparent carrier. Alternatively, the illumination may be created by an external device, i.e. an external light source, and the generated light may be coupled into the on-eye device via light-conducting leads. In this case the on-eye device does not need to contain a power management subsystem (i.e. a power interface, a power storage and possible some processing capabilities) or communication means.

Similarly, the power management subsystem for the on-eyelid device and/or the data transmission/communication means for the on-eyelid device may be incorporated in a separate device and connected via leads or wirelessly to the on-eyelid housing.

During anesthesia it may happen that the eyes roll back. To cope with this effect, the photosensor in the one-eyelid housing usually covers a large area to ensure the pupil is continuously in the field of view. The illumination means on the transparent carrier moves with the eye, so tracking of the position of the iris and pupil via tracking of the position of the on-eye device is straightforward and possible via, e.g., a separate light source, magnet or other means.

With regards to the materials to be used, this embodiment also has the advantage that the detector layer does not have to be transparent since incident light does not need to travel through the photosensor. This allows for a broader range of detector materials and detector patterns to be used but means that vision will be impaired, limiting the range of applications. Also, the fact that a device is placed on the eyelids makes applications such as sleep monitoring less straightforward.

After reflection by the eye the light needs to travel to the detector and needs to pass the eyelid. This will introduce some loss of spatial resolution, and signal loss due to scattering and absorption in the tissue, blood, eyelashes and possibly tape. However, if an array of photodetectors is used in the photosensor, each with a discrete outcome (yes/no over pupil), the effects will be minor. By the same rationale, the effect of local inhomogeneities in light output over the illumination area will be minor. The effects of tissue can be decreased by using IR light, the effects of variations in blood oxygenation can be decreased by using light at the isosbestic point of oxyhemoglobin/deoxyhemoglobin.

In an embodiment a single large area photodetector can be used in the photosensor in the on-eyelid housing and the illumination means can be integrated in a transparent carrier for being in contact with the eye. Thereby, the total amount of reflected light by the eye is measured as described above. The effects of absorption and scattering in the eyelids, eyelashes and tape can be larger in case an on-eyelid housing is used. This holds also for the effect of inhomogeneities in the output of the illumination means since the illumination means needs to be very homogeneous or the inhomogeneities should be constant so they can be corrected for in the calibration session.

In an embodiment the on-eye device can be simplified by producing light in an external device and guiding the light via light-guides to the on-eye device. The transparent carrier, i.e. the contact lens, can be used as waveguiding slab, i.e. by injecting light form the side of the lens, and subsequently out-coupling by scattering photonic features on the surface on the lens. This removes the needs for light emitters, power management subsystem and communication means in the on-eye device in comparison to some of the above-described embodiments. Thereby, the on-eye device becomes a completely passive conductor of light.

In an embodiment powering and/or communication means can be integrated in an additional device. The on-eyelid housing can be simplified by placing the power management subsystem and communication means in an external device with leads to the on-eyelid device. This way, the on-eyelid housing needs only to contain the photosensor.

In an embodiment the photosensor including the single large area photodetector may be integrated in an on-eyelid housing with an additional external light source. The external light source may be mounted at a distance or included in the on-eyelid housing to increase signal strength and therefore increase resolution and accuracy. Ambient light and light from the external light source travel through the device and the eye lid, reflect on the iris and sclera, travel again through the eye lid and is absorbed by the sensor in the device. The sensor contains a large area photodetector that measures the total reflected light.

The use of an on-eyelid housing makes the device less obtrusive for a user since the device is easy to apply and to remove, for instance via glasses, a holder or by using tape. Usually, there is no need to touch the eye during application and removal of the device. Thus the use of an on-eyelid housing only requires a simple design and can be efficiently manufactured, because there are fewer restrictions to the device. Also, connections for power and signals are easier to manufacture, since the device is on the eyelid so the strict spatial restrictions of a contact lens no longer apply, and there is no longer the semi-closed compartment created by the eyelid.

Scattering of light in the eyelids occurring due to the larger distance between the reflective surface (eye) and the sensor may be compensated by using collimated light or a collimator before the detector or by averaging the data so that temporal resolution is reduced. The problem that the eyes may roll back during anesthesia may be coped with by covering a large area with the photosensor to ensure the pupil is continuously in the field of view of by tracking the eye position in real-time.

Figure 13:
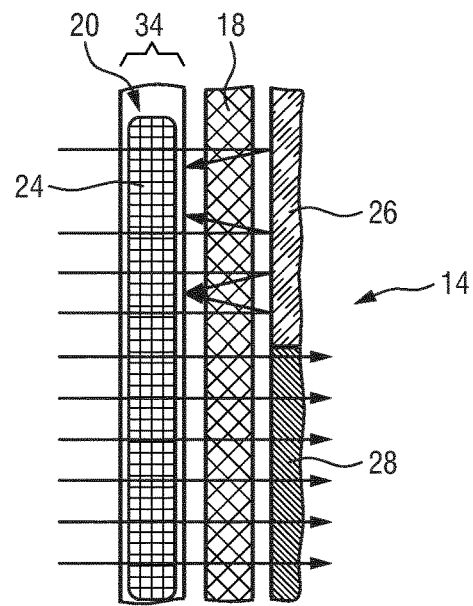
FIG. 13 schematically illustrates a device including a single large area photosensor in an on-eyelid housing device.

In an embodiment of a device 10d as illustrated in FIG. 13, a single large area photodetector 24 can be used in the photosensor 20 in the on-eyelid housing 34 so that incident light 16 can enter the eye 14 through the photosensor 20 and no illumination means are required.

Figure 14:
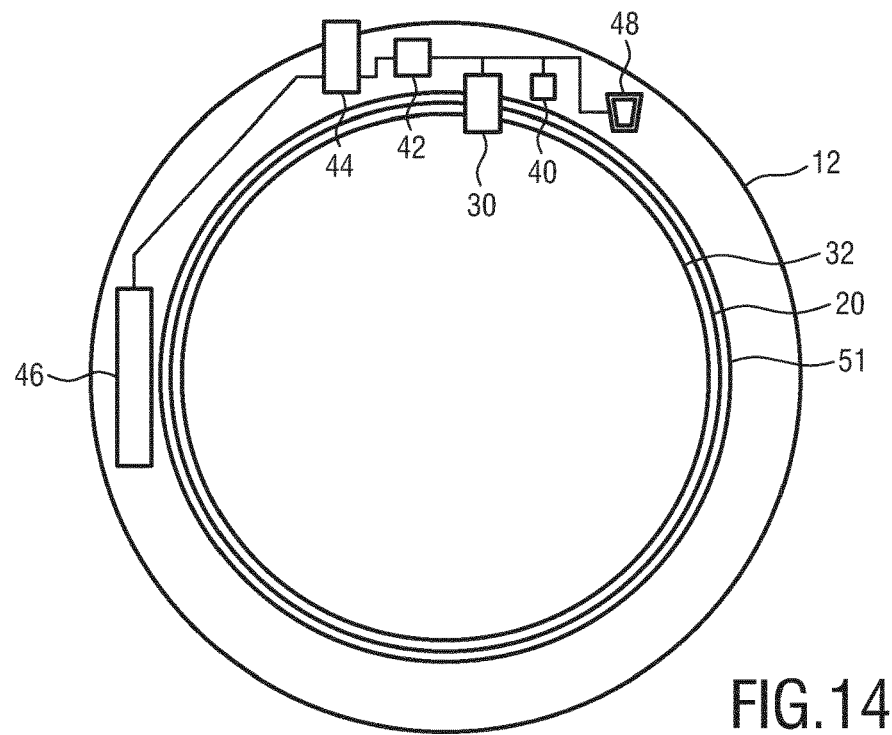
FIG. 14 schematically illustrates different optional and mandatory components of embodiments of devices according to the present invention.

FIG. 14 illustrates schematically different components that may be included in different embodiments of the device 10 in addition to the transparent carrier 12 and the photosensor 20. It is to be understood that the respective components may be present in different combinations. Also, it is to be understood that some components can also be included in an external housing such as an on-eyelid housing.

The illustrated device 10 includes a photosensor 20. The photosensor 20 may include a plurality of photodiodes representing photodetectors. The photodiodes may be arranged on and/or embedded within the transparent carrier 12. On the one hand, standard photodiodes can be used that detect both incident and reflected light. This is the easiest option for manufacturing. However, the sensitivity with respect to the reflected light is decreased since also incident light is detected. Thus, it is possible to add a non-translucent shielding layer to the photodetectors at the side of the eyelids. This layer may (partially) block the incident light, so that the reflected light is preferentially detected. Thereby, the sensitivity towards the reflected light may be increased.

It is also possible that the at least one photosensor 20 includes a single large area photodetector.

In an embodiment the at least one photosensor 20 may be tailored to detect optimally light of a specific color/wavelength. As outlined above, light that is reflected by the iris will be of a different spectrum than the incident light depending on the color of the iris. Thus, if a photosensor sensitive to a specific spectrum is used, the reflected light at an iris of a specific color will be detected more sensitively than light of another wavelength. Thereby, the sensitivity of the measurement can be improved. Thus, it is possible that there are specific devices for brown eyes, blue eyes etc.

Usually, the at least one photodetector 22 in a photosensor 20 is readout by readout electronics (may also be referred to as operating circuitry). The readout electronics allows reading out the signals provided by the at least one photodetector. In particular, the readout electronics includes the required wiring of the different components and any further necessary components such as capacitors, resistors etc. The readout electronics may drive the at least one photodetector. The readout electronics may perform some signal processing on the signals of the at least one photodetector.

Optionally, it may be possible to include a second photosensor 40 facing away from the eye for detecting an incident light intensity and correcting fluctuations in incident light reaching the eye. Such variations may include: variable light source, eye lid movement or changing blood volume in the eye lid. By determining a light intensity of the incident light, the sensitivity may be further increased as the intensity of the reflected light can be compared to the intensity of the incident light. It is also possible to make use of a second photosensor including a plurality of photodetectors. For instance, it may be possible to arrange two different rows of photodiodes on the transparent carrier. One row for detecting incident light and another row for detecting reflected light. This way sensitivity may be increased even more by correcting for local variations due to the light source, eyelids, eyelashes and tape.

Furthermore, the device may include a processor 42 for determining a pupil parameter and/or, based thereupon, a pain parameter and/or an analgesia parameter. The processor 42 may be represented by a microprocessor. The processor 42 processes and evaluates the light intensity, i.e. the output of the photosensor. In case the light intensity includes values (e.g. binary values) for a plurality of photodetectors in an array, i.e. corresponds to a two-dimensional light intensity distribution, the processor 42 may generate a 2D image of the eye showing an area of no or less reflected light, which corresponds to the pupil. Therefrom, a pupil parameter being indicative of a diameter of the pupil can be derived, e.g. via edge detection or comparable approaches. This way, the size and position of the pupil can be continuously monitored. Depending on the format of the output of the photosensor the processor 42 can be configured to perform an adequate processing.

Still further, the device 10 may comprise a light source corresponding to illumination means 30. The illumination means 30 may also be controlled by the processor 42. A light source can be integrated with the device in various configurations. For instance, an illumination means 30 may consist of a LED or an array of LEDs. Also, an illumination means may consist of an OLED unit (a single unit in various shapes and/or multiple units and/or an array of OLEDs) a laser or multiple lasers. Also, the illumination means may be incorporated by an illumination layer (e.g. an array of LEDs or contact lens being used as a waveguiding slab; i.e. by injecting light form the side of the lens, and subsequently out-coupling by scattering photonic features on the surface on the lens). Alternatively, discrete light sources may be used, so that only a small portion of the field of view of the photodetectors is blocked by the illumination sources.

Preferably, the light is directional towards the eye, and the illumination means is transparent for the reflected light so it may reach the photosensor. When the illumination means 30 emits infrared light, the application becomes independent of the iris color, since the pupil is easily visible under infrared light. The pupil does not reflect IR light, whereas all colored irises (including dark brown) reflect IR light. IR light also does not induce the pupil light reflex.

The use of illumination means 30 has the effect that light is always available for the pupillometry measurement and that the effect of scattering of light in the eye lids is decreased since much of the incident light does not travel through the eyelids. The eyelids and (in the OR) applied tape block incident light. If a large fraction of the light is thus blocked, the photodetector may not be sensitive enough to detect changes in reflected light due to pupil size variations. Implementing an illumination means eliminates this problem by the application of extra artificial light on the eye, increasing the spatial and temporal resolution. The illumination means 30 may, e.g., allow the device 10 to work also in environments with lower ambient light level, in which otherwise not enough light would penetrate the eyelids for a reliable measurement.

Furthermore, the use of illumination means 30 may allow exploiting the pupillary light reflex. By making use of illumination means directly on the eye, the pupil diameter may be changed via the pupillary light reflex, thus interfering with the pupillometry measurement. Hence, if the light intensity provided by the illumination means 30 is of sufficient strength, additional information can be obtained from the device such as how the patient reacts to a provided stimulus of intense light, as in the standard pupillary light reflex diagnostic tool. This may be used in the emergency room for assessing brain stem function, but cannot be done in the OR as there is no way to "read" the reaction of the pupil unless the eye is opened. Additionally, a programmed series of light pulses can be provided and the reaction of the pupil measured to provide additional information on the status of the patient. Furthermore, if the device is used for sleeping patients, the sleeping pattern may be influenced by the incident artificial light. Therefore, the strength and/or wavelength should be chosen carefully, such that the pupillometry measurement is still feasible. The use of infrared light will eliminate (most of) these drawbacks.

In an embodiment the illumination means may be configured to generate IR and visible light. IR light gives the best results for pupillometry because the reflection is independent of the iris color. Further, IR light does not alter the pupil diameter via the pupil light reflex. The pupil will react to visible light (VIS), which may be used for calibration purposes and for analysis of the pupil light reflex. Thus, the illumination means may include two light sources or a combined light source to provide both reliable calibration (with VIS) and measurement (IR), which also allows performing the pupil light reflex neurological examination with closed eyes.

In an embodiment, the illumination means, may be used intermittently. Using pulsed IR light and correcting the value with the illumination means for the value using only ambient light, higher accuracy is achieved at the expense of lower temporal resolution.

Still further, the device 10 may include a shielding layer 32 in the transparent carrier 12. This shielding layer 32 corresponds to a layer of non-translucent material and blocks incident light from entering the eye. The material of the shielding layer should block the incident light completely. Thus, any absorbing or reflecting material may be used, preferably in the form of a coating. In other embodiments it is possible that the shielding layer is semi-transparent, i.e. blocks incident light but passes light after a reflection at the eye, e.g. in case a photosensor in an external housing is used. Also, it may be possible that the shielding layer 32 corresponds to a plurality of individual small shielding elements at single photodetectors.

An advantage of the use of a shielding layer 32 in combination with illumination means 30 is that there are no light variations due to movement of the staff in the OR (which can cause, e.g., shadows), eyelid variations, flickering ambient light and/or tape used to tape eyes shut etc. Further advantages may include that all light detected by the photosensor is reflected light from the eye so that a background signal in the photosensor is minimized and that an adjustable and constant light output is provided so that there are no variations in incident light. Further, variations over the illumination area can easily be corrected for if these are constant and an improved spatial resolution due to minimized light scattering. Still further, if an on-eyelid device as described above is used, the reflected light has to cross the eyelids and will be attenuated, whereas any "false" light may reach the detector without attenuation. This will lead to a high background value and effect of variations. The shielding layer can help to overcome these issues.

Since the patients are usually sedated in the OR, it will usually not be a problem that the vision is fully impaired in the monitored eye. Variations in light intensity over the illumination surface that are constant or fluctuating in a predictive way can be corrected via signal processing. The effect that the artificial light source may influence the pupil size (pupil light reflex) can be reduced by using infrared light. Also, it may be possible to exploit and/or test this effect by giving a short pulse of visible light.

The device 10 may also include a power interface 44. For instance, the photosensor 20, the illumination means 30 as well as other components may be powered by an RF antenna representing the power interface 44, which can be incorporated in the transparent carrier. An RF transmitter at a preferred maximum distance in the order of a few cm can then be used for transmitting power wirelessly. Such a transmitter may, e.g. be arranged on the nose or the forehead of a patient. This method can be used to provide power for an indefinite time.

In an embodiment, the electric current generated by the photodetector can also be used for powering the device. In this case, a power management system is expected to be equipped with components for retrieving the charge generated by the detector itself.

Alternatively or additionally, a power storage unit 46 may be included. For instance, a thin film battery may be used. In spite of a limited battery life, a completely self-sufficient operation can be obtained thereby.

Still further, the device 10 may include a communication interface 48 via which the determined light intensity and/or a parameter derived therefrom can be communicated to an external processing or display device such as a computer. For instance, the information on the detected light levels per photodiode (i.e. the two-dimensional light intensity distribution when an array of photodetectors is used) may be transmitted via RF communication such as NFC. For this, the communication interface may include an antenna and a transmitter. It may, however, also be possible that a wired transmission is used.

It may be possible that the power interface 44 and the communication interface 48 make use of the same antenna and further electronics.

It is possible that the processor 42, the illumination means 30, the power interface 44, the power storage unit 36 and/or the communication interface are arranged on the transparent carrier 12 as illustrated in FIG. 14. It is, however, also possible that one or more of the units are partly or entirely arranged external to the device 10 and connected to the device via a wireless or wired connection. It is to be understood that the continuous pupillometry approach with closed eyes of the present invention may also be performed in a wired operation. If the device 10 is used on a patient being under the effect of anesthesia, the patient will usually be relatively stationary so that a wired operation is not a problem.

As an alternative or in addition to the illumination means 30, it is possible to use an external light source, i.e. a light source located in front of the eyelid, e.g. in an on-eyelid housing.

Figure 15:
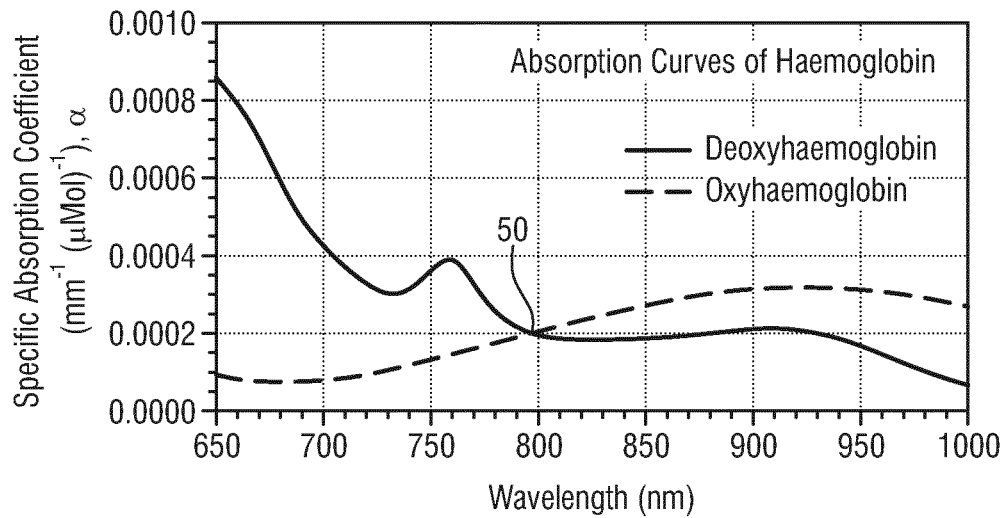
FIG. 15 schematically illustrates the isosbestic point of light absorption of hemoglobin and deoxyhemoglobin.

In particular the use of an external light source may make it possible to obtain further information by illuminating the eye with light of a predefined wavelength. For instance, light of a wavelength corresponding to the isosbestic point of the light absorption of hemoglobin and deoxyhemoglobin can be used. This concept is illustrated with in FIG. 15. If light of a specific color/wavelength is emitted which optimally penetrates the eyelids. It is known that light of 600-800 nm penetrates skin the most, so a red laser or LED would be preferred for an external light source. Additionally, however, hemoglobin in the blood is a known absorber of light. This will create variations in the incident light intensity over the eye due to the location of blood vessels in the eyelids and over time as the oxygenation level may vary during the procedure. This is a confounding factor that may create noise in the measurements. Thus, the incident light will be affected by blood flow as a result of changing light absorption levels. This effect may be avoided or minimized by selecting a proper wavelength of the external light source, e.g. choosing light of approx. 800 nm at which absorption by (oxy-) hemoglobin (HB—$O_2$) and deoxyhemoglobin (HB) is equal (isosbestic point 50). In other words, 'noise' induced by pulsation may be making use of prevented so that the detected light intensity variations are only related to the pupil diameter.

In another embodiment, this effect may also be obtained if a light source is used that emits white light by making use of a band-pass (color) filter that passes only light at the isosbestic point 50 for filtering the incident light or the reflected light.

Alternatively, this effect of different light absorption may also be exploited, e.g. by extracting the heart rate from measured fluctuations.

Still further, it is possible to sequentially operate on and off the isosbestic point 50 to allow for alternating operation of pupillometry and oxygenation monitoring. In other words, a duty cycling is applied in which the pupil diameter is measured at a wavelength at the isosbestic point and the heart rate is measured at a wavelength other than the isosbestic point. In particular, in the infrared region (e.g. wavelength >~850 nm) the difference between oxyhemoglobin and deoxyhemoglobin becomes significant. For instance, it may be possible to operate ten seconds for pupillometry (at the isosbestic point) and then shift the wavelength out of the isosbestic point for oxygenation monitoring for fifty seconds (time scales are arbitrary and only meant as an example). Alternatively, it may also be possible to make use of a light source emitting white light and two different types of photodetectors being dedicated to two different wavelengths corresponding to the isosbestic point and the oxygenation detection wavelength, respectively. This will allow simultaneous operation of both features mentioned above.

It may also be possible to make use of some of the above-outlined effects by including illumination means 30 on the transparent carrier 12 configured to emit light at a certain wavelength. In case of a photosensor in an on-eyelid housing the light will travel through the eyelid. Also if the photosensor is also included in the transparent carrier, the reflection at the eye may cause some interference with blood in the eye so that it is also possible to derive further information therefrom.

In a preferred embodiment, the device is initially calibrated for a given subject, since the incident light level, light transmission and diffusion through the eyelid, the 'tone' of the sclera and the iris color have an influence on the total reflected light intensity. In case of using the infrared light spectrum, the device is expected to be less sensitive towards the iris color differences.

Usually, the device of the present invention will need to be calibrated in order to provide accurate pupil size measurements. The use of an external light source located in front of the eyelid of the subject may allow calibrating the photodetectors. For instance, a light source capable of sending many small laminated bundles of light may be used. This way, during calibration, each individual photodetector or each cluster of photodetectors can be calibrated (using the readings of the device) so that reflected light through the eyelids and tape is equal over the complete eye. This will improve the accuracy of the pupil size measurement. It may also be possible to calibrate the light source. Additionally, using a normal or laminated light source capable of sending light of different colors/wavelengths may allow determining an optimal wavelength of light providing the most sensitive and accurate reading of the device for that patient (depending on the patient's eye color).

In an embodiment, the device 10 further includes a filter 51 for passing light of a predefined wavelength as described above. The filter 51 may be integrated in the transparent carrier 12.

Figure 16:
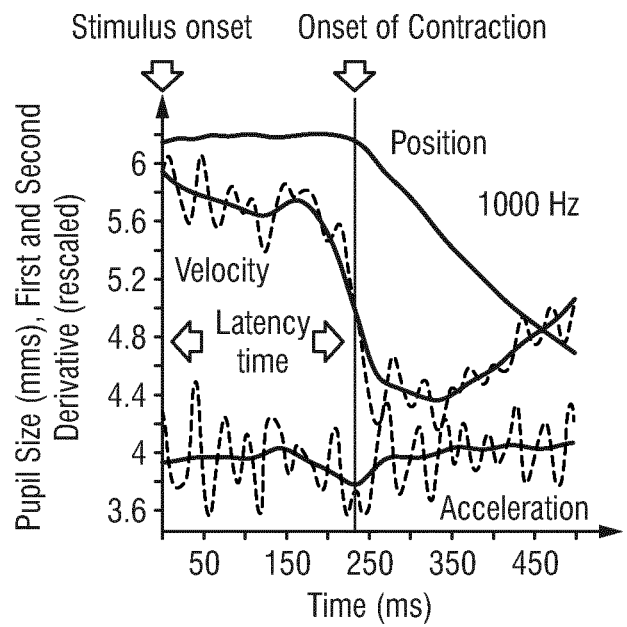
FIG. 16 schematically illustrates the latency time of a pupillary response of a subject.
Figure 17:
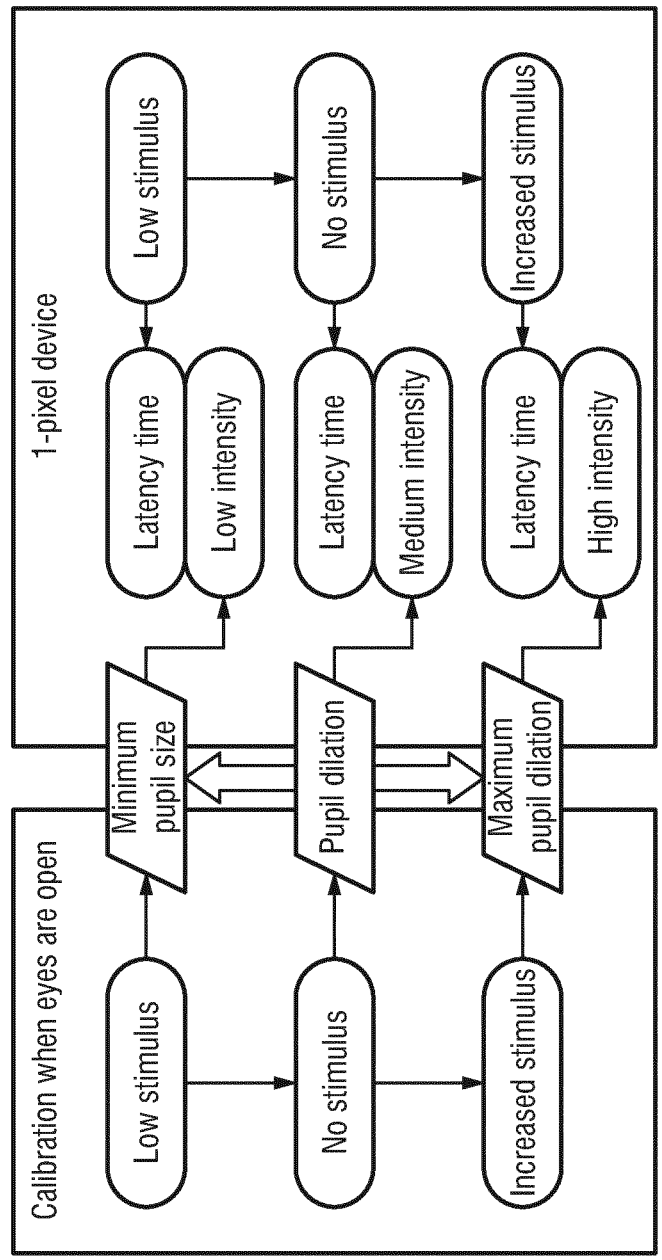
FIG. 17 schematically illustrates a calibration method for being carried out by means of a device according to the present invention.

Another approach to calibration is schematically illustrated in FIGS. 16 and 17. Since the total reflected light intensity may be affected by the differences of optical properties of sclera, iris and the eyelid of different subjects, a calibration step is executed for a given individual under conditions similar to the actual use case (e.g. with closed eyes prior to anesthesia). During calibration the actual diameter of the pupil cannot be assessed. One option to cope with this is to measure the pupil diameter under normal and strongly stimulated (with an external light source or with appropriate illumination means) conditions, with open eyes first and with closed eyes. In the open-eye configuration, the pupil diameter response is measured using a standard pupillometry device. This result is considered the expected response for the closed eyes configuration. After this, the pupil diameter in the closed-eye configuration is measured with ambient light, prior to and directly after a high light intensity signal. Since there is a latency time between the stimulus and the pupil response as illustrated in FIG. 16 (cf. Investigative Ophthalmology & Visual Science April 2003, Vol. 44, 1546-1554. doi:10.1167/iovs.02-0468), the pupil is still assumed to be small, even when the stimulus (high intensity light) has been removed. In particular, this calibration approach provides accurate results in case a single large area photodetector is included in the photosensor. This single large area photodetector allows for a high sampling rate, so the pupil diameter can be measured within the latency time, but with ambient light conditions. These signals can now be correlated to the open-eye configuration and used for calibration.

Figure 18:
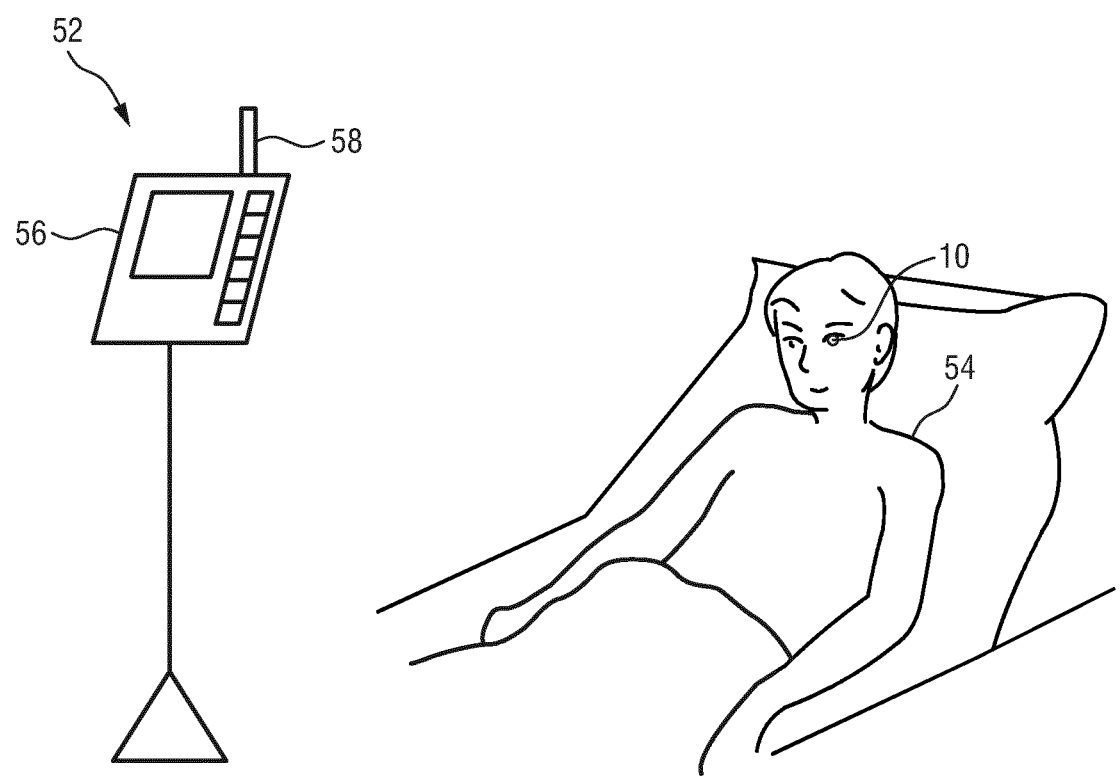
FIG. 18 schematically illustrates a system according to an aspect of the present invention.

FIG. 18 schematically illustrates a system 52 for monitoring a patient 54 according to an aspect of the present invention. The system 52 includes the above-described device 10. The device 10 is applied to an eye of the patient 44. The device 10 is in communication with a monitoring interface 56 via a communication interface 58. The monitoring interface 56 may, e.g. correspond to a computer or display, for providing information to a physician and/or anesthesiologist. The system 52 may, e.g., be put to use in an OR setting. An anesthesiologist may use the provided information for monitoring the patient and adjust the administration of drugs based thereupon.

In an embodiment light intensity determined by the device of the present invention may by used together with one or more vital signs (heart rate, blood pressure, SCR, heart rate variability, ECG, EEG) of the patient, patient characteristics (age, weight, sex, medical history, medication status) and/or population values. Thereby, the depth of anesthesia or analgesia and/or a pain parameter may be calculated with a higher significance.

In another embodiment devices of the present invention may be applied to both eyes of a subject. Comparing the pupil size and oscillation between right and left eye and/or differences in the reaction to a light stimulus will provide additional information on the status of the patient.

Yet another application area of a device of the present invention may also be sleep monitoring. Using a fixed position for the transparent carrier, the device may also provide information on the exact location of the pupil (including saccadic motion) if a proper photodiode design is chosen. A prerequisite is that the transparent carrier is rather flexible so that the eye can move under a static transparent carrier. This additional information may be useful in a range of applications. Especially sleep analysis will be benefit from this as it allows quantitative REM sleep analysis (pupil movements are indicative of sleep phases).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Any reference signs in the claims should not be construed as limiting the scope.

The invention claimed is:

1. A device configured to monitor an eye of a subject, the eye comprising an iris and a pupil, the device comprising:
   a transparent carrier configured to contact with the eye of the subject; and
   a photosensor, facing the eye of the subject, configured to receive light reflected from the eye of the subject, and determine a light intensity of the received light, wherein the photosensor is arranged on the transparent carrier and includes a plurality of photodetectors spaced apart from one another for allowing incident light to pass between the photodetectors to enter the eye of the subject, and arranged in a plurality of concentric circles substantially covering the iris and the pupil of the eye of the subject.

2. The device as claimed in claim 1, wherein the transparent carrier includes a filter configured to pass light of a predefined wavelength.

3. The device as claimed in claim 2, wherein the predefined wavelength corresponds to an isosbestic point of light absorption of oxygenated hemoglobin and deoxyhemoglobin in blood of the subject.

4. The device as claimed in claim 1, further comprising: a processor configured to determine a pupil parameter indicative of a size of the pupil of the subject based on the determined light intensity.

5. The device as claimed in claim 4, wherein the processor is further configured to determine an analgesia parameter indicative of a depth of analgesia of the subject based on the pupil parameter.

6. The device as claimed in claim 4, wherein the processor is configured to determine a calibration parameter for the subject by determining a pupil diameter of the pupil in a normal state and in a stimulated state.

7. The device as claimed in claim 1, further comprising: a second photosensor facing away from the eye of the subject configured to receive incident light and determine a light intensity of incident light.

8. The device as claimed in claim 1, wherein the transparent carrier further comprises:
   a thin-film battery configured to enable a self-sufficient operation of the device; and
   a wireless power interface configured to receive power wirelessly.

9. The device as claimed in claim 1, wherein an electrical current output of the photosensor is used for powering the device.

10. The device as claimed in claim 1, wherein the transparent carrier is configured to emit light into the eye of the subject.

11. The device as claimed in claim 10, wherein the transparent carrier further comprises: a shielding layer configured to block incident light from entering the eye of the subject.

12. The device as claimed in claim 10, wherein the illumination means is configured to emit light at an isosbestic point of light absorption of oxygenated hemoglobin and deoxyhemoglobin in blood of the subject.

13. A system configured to monitor for monitoring a pain level of a subject, the system comprising:
   the device as claimed in claim 1 applied to the eye of the subject;
   a communication interface configured to communicate with the device and receive from the device of the light intensity and a monitoring parameter determined based on the light intensity; and
   a monitoring interface configured to determine information based on the light intensity and the monitoring parameter.

14. A method for monitoring an eye of a subject, the eye comprising an iris and a pupil, the method comprising:
   receiving light reflected from the eye of the subject by means of a plurality of photodetectors spaced apart from one another for allowing incident light to enter the eye of the subject, wherein the plurality of photodetectors is arranged in a plurality of concentric circles substantially covering the iris and the pupil of the eye of the subject;
   determining a light intensity of the received light;
   determining a pupil parameter being indicative of a size of a pupil of the subject based on the determined light intensity; and
   determining an analgesia parameter being indicative of a depth of analgesia of the subject based on the pupil parameter.

15. A non-transitory storage medium storing instructions readable and executable by an electronic data processing device to perform a method for monitoring an eye of a subject, the eye comprising an iris and a pupil, the non-transitory storage medium comprising:
   instructions for receiving light reflected from the eye of the subject by means of a plurality of photodetectors spaced apart from one another for allowing incident light to enter the eye of the subject, wherein the plurality of photodetectors is arranged in a plurality of concentric circles substantially covering the iris and the pupil of the eye of the subject;
   instructions for determining a light intensity of the received light;
   instructions for determining a pupil parameter being indicative of a size of a pupil of the subject based on the determined light intensity; and
   instructions for determining an analgesia parameter being indicative of a depth of analgesia of the subject based on the pupil parameter.

* * * * *